_(12)_ United States Patent
Schultz Hume et al.

US009102597B2

(10) Patent No.: US 9,102,597 B2
(45) Date of Patent: Aug. 11, 2015

(54) INDANE BISPHENOLS, POLYMERS DERIVED THEREFROM, AND METHODS OF USE THEREOF

(75) Inventors: Laura G. Schultz Hume, Newburgh, IN (US); Shubashree Swaminathan, Bangalore (IN); Ganapathy Bhotla Venkata Ramanarayanan, Bangalore, IN (US)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 13/604,419

(22) Filed: Sep. 5, 2012

(65) Prior Publication Data

US 2014/0061533 A1    Mar. 6, 2014

(51) Int. Cl.
| | |
|---|---|
| C08G 61/02 | (2006.01) |
| C07C 39/17 | (2006.01) |
| C08G 64/16 | (2006.01) |
| C08L 69/00 | (2006.01) |
| C08G 64/06 | (2006.01) |
| C08L 83/10 | (2006.01) |
| C08G 63/193 | (2006.01) |
| C08G 63/64 | (2006.01) |
| C08G 64/14 | (2006.01) |
| C07C 37/20 | (2006.01) |
| C08G 77/448 | (2006.01) |

(52) U.S. Cl.
CPC ............ *C07C 39/17* (2013.01); *C07C 37/20* (2013.01); *C08G 63/193* (2013.01); *C08G 63/64* (2013.01); *C08G 64/06* (2013.01); *C08G 64/14* (2013.01); *C08G 64/1691* (2013.01); *C08L 69/00* (2013.01); *C08L 83/10* (2013.01); *C07C 2102/08* (2013.01); *C08G 77/448* (2013.01)

(58) Field of Classification Search
USPC .................... 528/86, 201, 196, 198
See application file for complete search history.

(56) References Cited

U.S. PATENT DOCUMENTS

| | | | |
|---|---|---|---|
| 3,516,968 A | 6/1970 | Moore | |
| 3,546,165 A | 12/1970 | Morgan | |
| 4,129,612 A | 12/1978 | Serini et al. | |
| 5,703,197 A | 12/1997 | Gordon et al. | |
| 5,777,063 A | 7/1998 | Gordon et al. | |
| 5,883,218 A | 3/1999 | Gordon et al. | |
| 6,093,785 A * | 7/2000 | Gordon et al. | ............... 528/196 |
| 6,174,987 B1 | 1/2001 | Gordon et al. | |
| 7,112,644 B2 | 9/2006 | Morishita et al. | |
| 7,244,804 B2 | 7/2007 | Ikeda et al. | |
| 7,678,455 B2 | 3/2010 | Takada et al. | |
| 8,064,140 B2 | 11/2011 | Hoeks et al. | |
| 8,119,762 B2 | 2/2012 | Crawford et al. | |
| 2006/0004151 A1 | 1/2006 | Shaikh et al. | |
| 2009/0176946 A1 | 7/2009 | Kusters et al. | |
| 2009/0186966 A1 | 7/2009 | Gallucci et al. | |
| 2010/0015551 A1* | 1/2010 | Mihara et al. | ............. 430/280.1 |
| 2010/0152416 A1 | 6/2010 | Bhotla et al. | |
| 2011/0097566 A1 | 4/2011 | Higaki | |
| 2011/0183120 A1 | 7/2011 | Sharygin et al. | |
| 2014/0296580 A1 | 10/2014 | Hume et al. | |

FOREIGN PATENT DOCUMENTS

| | | | |
|---|---|---|---|
| EP | 2145880 | 1/2010 | |
| EP | 2137227 | 9/2011 | |
| JP | 2010105917 | 5/2010 | |
| JP | 2010202778 | * 9/2010 | ............. C07C 69/54 |
| JP | 2011178873 | 9/2011 | |
| JP | 2011219667 | 11/2011 | |
| JP | 4840074 | 12/2011 | |
| WO | 99/06464 | 2/1999 | |
| WO | 2010/101033 | 9/2010 | |

OTHER PUBLICATIONS

Morgan, P.W. "Aromatic Polyesters with Large Cross-Planar Substituents" Macromolecules 1970, vol. 3, No. 5, pp. 536-544.
Yang, et al., "Life cycle assessment of mobile phone housing" Journal of Environmental Sciences, Issue 1, vol. 16, pp. 100-103, Apr. 8, 2005.
PCT/US2013/058215 International Search Report and Written Opinion dated Nov. 8, 2013 (4 pages).
United States Patent Office Action for U.S. Appl. No. 14/305,984 dated Jul. 30, 2014 (7 pages).
International Preliminary Report on Patentability issued in International Patent Application No. PCT/US2013/058215 (Mar. 10, 2015).

* cited by examiner

*Primary Examiner* — Shane Fang
(74) *Attorney, Agent, or Firm* — Michael Best & Friedrich LLP

(57) ABSTRACT

Indane bisphenol monomer units, and polymers derived from such monomer units are provided. Also provided are blends including such polymers, articles made from such polymers and blends, methods of using such monomers, polymers, and blends, and processes for preparing such monomers, polymers, and blends.

31 Claims, No Drawings

INDANE BISPHENOLS, POLYMERS DERIVED THEREFROM, AND METHODS OF USE THEREOF

TECHNICAL FIELD

The present disclosure relates generally to indane bisphenol monomer units, polymers derived from the monomer units, and blend compositions thereof.

BACKGROUND

Polycarbonates are polymers that may be derived from bisphenols and phosgene, or their derivatives. They are useful for forming a wide variety of products, such as by molding, extrusion, and thermoforming processes. Such products include articles and components that include auto parts, electronic appliances and cell phone components. Because of their broad use, particularly in electronic applications and auto part applications, the desired properties of polycarbonates include high impact strength and toughness, heat resistance, weather and ozone resistance, and good ductility. It is also desirable that polycarbonates exhibit physical properties amenable to efficient and economic manufacturing processes.

Certain indane bisphenol monomers, such as 4,4'-(2,3-dihydro-1H-indene-1,1-diyl)diphenol, have been used to prepare high heat polycarbonates. Such indane bisphenols are, however, prone to chemical reaction at the benzylic position (e.g., deprotonation or oxidation), which in turn adversely impacts the properties and functional lifetime of the polycarbonates derived therefrom.

Indanone bisphenols, such as 3,3-bis(4-hydroxyphenyl)-2-phenylisoindolin-1-one, lack benzylic hydrogens, and as a result avoid the stability issues of indane bisphenols such as 4,4'-(2,3-dihydro-1H-indene-1,1-diyl)diphenol. Consequently, indanone bisphenols have largely replaced indane bisphenols as the preferred monomer type to impart high heat resistance to polycarbonates.

Nonetheless, there still exists a need for improved monomers and polycarbonates, and high heat polycarbonates in particular, demonstrating one or more of acceptable impact strength, heat resistance, weatherability, ductility, and processability.

SUMMARY

Disclosed herein are indane bisphenol monomer units, and polymers derived from such monomer units. Also disclosed herein are blends comprising such polymers, articles comprising such polymers and blends, methods of using such monomers, polymers, and blends, and processes for preparing such monomers, polymers, and blends.

In one aspect, disclosed herein are indane bisphenol monomer units having formula (I),

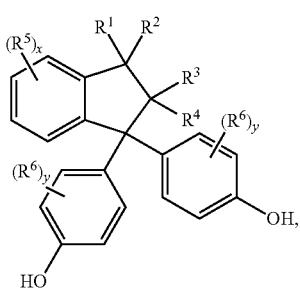

(I)

wherein $R^1$, $R^2$, $R^3$, and $R^4$ are each independently hydrogen, $C_1$-$C_6$ alkyl, $C_3$-$C_8$ cycloalkyl, aryl, or arylalkyl, provided that at least one of $R^1$, $R^2$, $R^3$, and $R^4$ is other than hydrogen;

$R^5$ and $R^6$, at each occurrence, are each independently halogen, $C_1$-$C_6$ alkyl, or $C_3$-$C_8$ cycloalkyl; and x and y, at each occurrence, are each independently 0, 1, 2, 3, or 4.

In certain embodiments, the monomer unit of formula (I) is 4,4'-(3,3-dimethyl-2,2-dihydro-1H-indene-1,1-diyl)diphenol; 4,4'-(3-methyl-2,2,3-trihydro-1H-indene-1,1-diyl)diphenol; 4,4'-(2,3,3-trimethyl-2-hydro-1H-indene-1,1-diyl)diphenol; or 4,4'-(2,2,3,3-tetramethyl-1H-indene-1,1-diyl)diphenol. In certain embodiments, the monomer unit of formula (U) is 4,4'-(3,3-dimethyl-2,2-dihydro-1H-indene-1,1-diyl)diphenol. In certain embodiments, the monomer unit of formula (I) is 4,4'-(3-methyl-2,2,3-trihydro-1H-indene-1,1-diyl)diphenol.

In another aspect, disclosed herein are polymers comprising repeating units derived from indane bisphenols of formula (I).

In certain embodiments, the polymer comprises repeating units derived from monomer units having formula (II), also referred to herein as 4,4'-(3,3-dimethyl-2,2-dihydro-1H-indene-1,1-diyl)diphenol,

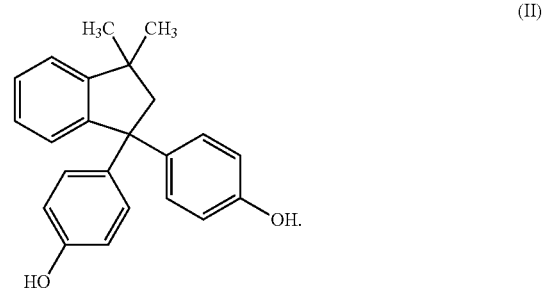

(II)

In certain embodiments, the polymer comprises repeating units derived from monomer units having formula (III), also referred to herein as 4,4'-(3-methyl-2,2,3-trihydro-1H-indene-1,1-diyl)diphenol,

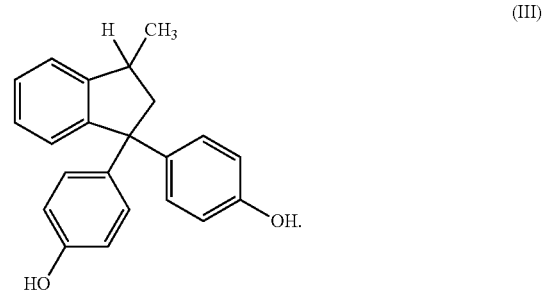

(III)

In certain embodiments, the polymer comprises repeating units derived from monomer units having formula (IV), also referred to herein as 4,4'-(2,3,3-trimethyl-2-hydro-1H-indene-1,1-diyl)diphenol,

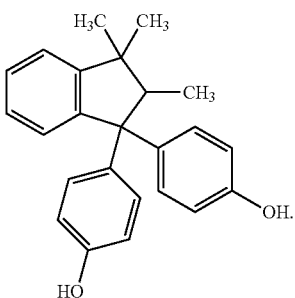

(IV)

In certain embodiments, the polymer comprises repeating units derived from monomer units having formula (V), also referred to herein as 4,4'-(2,2,3,3-tetramethyl-1H-indene-1,1-diyl)diphenol,

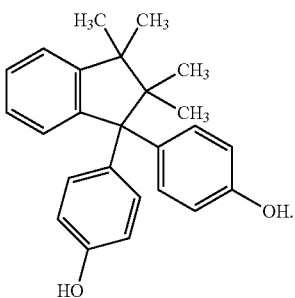

(V)

In certain embodiments, the polymer further comprises (i) repeating units derived from one or more monomers having the structure HO-$A_1$-$Y_1$-$A_2$-OH wherein each of $A_1$ and $A_2$ comprise a monocyclic divalent arylene group, and $Y_1$ is a bridging group having one or more atoms; (ii) repeating units derived from one or more monomers having the structure

wherein each $R_h$ is independently a halogen atom, a $C_1$-$C_{10}$ hydrocarbyl, or a halogen substituted $C_1$-$C_{10}$ hydrocarbyl, and n is 0 to 4; or (iii) one or more polyester repeating units having the structure

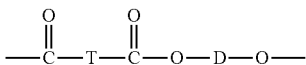

wherein D comprises one or more alkyl containing $C_6$-$C_{20}$ aromatic group(s), or one or more $C_6$-$C_{20}$ aromatic group(s), and T comprises a $C_6$-$C_{20}$ aromatic group. In certain embodiments, the repeating units derived from (i), (ii), and/or (iii) are derived from monomer units other than a monomer unit of formula (I).

In certain embodiments, the polymer is free of halogen atoms.

In certain embodiments, the polymer comprises an end cap group, wherein at least one end cap group is derived from p-cumylphenol, t-butylphenol, 4-hydroxybenzonitrile, or phenol.

In certain embodiments, the polymer has a weight average molecular weight ranging from about 15,000 to about 50,000 g/mol [±1,000 g/mol]. The polymer may have a polydispersity ranging from about 2.0 to about 7.0. The polymer may have a glass transition temperature ranging from about 150° C. to about 220° C.

In certain embodiments, the polymer is a homopolycarbonate, a copolycarbonate, a polyester, or a polycarbonate-polyester.

In certain embodiments, the polymer comprises repeating units derived from 2,2-bis(4-hydroxyphenyl)propane (bisphenol-A).

In certain embodiments, the polymer comprises more than 15 mole percent structural units derived from monomer units of formula (I), more than 30 mole percent structural units derived from monomer units of formula (I), or more than 40 mole percent structural units derived from monomer units of formula (I). In certain embodiments, the polymer comprises more than 15 mole percent structural units derived from monomer units of formula (I), and the remainder of the structural units are derived from 2,2-bis(4-hydroxyphenyl)propane (bisphenol-A). The monomer units of formula (I) may be 4,4'-(3,3-dimethyl-2,2-dihydro-1H-indene-1,1-diyl)diphenol. The monomer units of formula (I) may be 4,4'-(3-methyl-2,2,3-trihydro-1H-indene-1,1-diyl)diphenol.

In certain embodiments, the polymer is made by a melt process. In other embodiments, the polymer is made by an interfacial polymerization process.

In another aspect, disclosed herein are blend compositions comprising: (i) a first polymer (A) having repeating units derived from a monomer of formula (I); and (ii) a second polymer (B) which is different from polymer (A). The monomer of formula (I) may be 4,4'-(3,3-dimethyl-2,2-dihydro-1H-indene-1,1-diyl)diphenol. The monomer of formula (I) may be 4,4'-(3-methyl-2,2,3-trihydro-1H-indene-1,1-diyl)diphenol.

In certain embodiments, polymer (A) is a copolycarbonate of 4,4'-(3,3-dimethyl-2,2-dihydro-1H-indene-1,1-diyl)diphenol and bisphenol-A. In certain embodiments, polymer (A) is a copolycarbonate of 4,4'-(3-methyl-2,2,3-trihydro-1H-indene-1,1-diyl)diphenol and bisphenol-A.

In certain embodiments, polymer (B) is derived from monomer units other than monomer units of formula (I).

In certain embodiments, polymer (B) may be a vinyl polymer, a rubber-modified graft copolymer, an acrylic polymer, a polyacrylonitrile, a polystyrene, a polyolefin, a polyester, a polyesteramide, a polysiloxane, a polyurethane, a polyamide, a polyamideimide, a polysulfone, a polyepoxide, a polyether, a polyimide, a polyetherimide, a polyphenylene ether, a polyphenylene sulfide, a polyether ketone, a polyether ether ketone, an ABS resin, an ASA resin, a polyethersulfone, a polyphenylsulfone, a poly(alkenylaromatic) polymer, a polybutadiene, a polyacetal, a polycarbonate, a polyphenylene ether, an ethylene-vinyl acetate copolymer, a polyvinyl acetate, a liquid crystal polymer, an ethylene-tetrafluoroethylene copolymer, an aromatic polyester, a polyvinyl fluoride, a polyvinylidene fluoride, a polyvinylidene chloride, tetrafluoroethylene, a polylactide, a polylactic acid (PLA), a polycarbonate-polyorganosiloxane block copolymer, or a copolymer comprising: (i) an aromatic ester, (ii) an estercarbonate, and (iii) carbonate repeat units.

In certain embodiments, the blend composition may further include at least one additive. In certain embodiments, the additive may be an impact modifier. The impact modifier may include polycarbonate-polysiloxane copolymers, acrylonitrile-butadiene-styrene (ABS) polymers, methacrylate-butadiene-styrene (MBS) polymers, acrylate polymers, and combinations thereof. In certain embodiments, the additive may a UV stabilizer. The UV stabilizer may include 2-(2'-hydroxyphenyl)-benzotriazoles. In one embodiment, the UV stabilizer is 2-(2H-benzotriazole-2-yl)-4,6-bis(1-methyl-1-phenyl-ethyl)phenol.

In another aspect, disclosed herein are articles comprising the polymers and blends. The article may be selected from automotive bumpers, other automotive exterior components, automobile mirror housings, automobile wheel covers, automobile instrument panels and trim, automobile glove boxes, automobile door hardware and other interior trim, automobile exterior lights, automobile parts within the engine compartment, plumbing equipment, valves and pumps, air conditioning heating and cooling parts, furnace and heat pump parts, computer parts, electronics parts, projector parts, electronic display parts, copier parts, scanner parts, electronic printer toner cartridges, hair driers, irons, coffee makers, toasters, washing machines, microwaves, ovens, power tools, electric components, lighting parts, dental instruments, medical instruments, cookware, medical instrument trays, animal cages, fibers, laser welded medical devices, and fiber optics.

In another aspect, disclosed herein is a process for preparing an indane bisphenol of formula (I). The process may include treating a compound of formula (VI) with at least two equivalents of a phenol of formula (VII) in the presence of 3-mercaptopropionic acid and sulfuric acid,

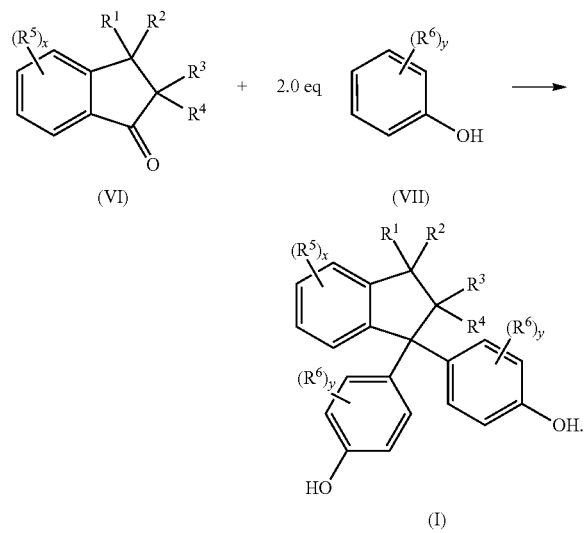

The compound of formula (VI) may be prepared by a process comprising treating a compound of formula (VIII) with a compound of formula (IX) in the presence of aluminum chloride, followed by quenching with a compound of formula (X),

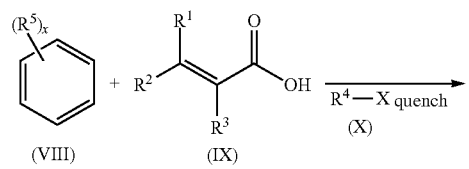

-continued

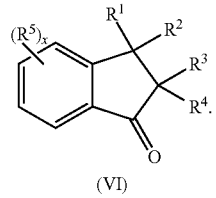

In certain embodiments, the process may be used to prepare 4,4'-(3,3-dimethyl-2,2-dihydro-1H-indene-1,1-diyl)diphenol or 4,4'-(3-methyl-2,2,3-trihydro-1H-indene-1,1-diyl)diphenol.

The compounds, compositions, methods, and processes are further described herein.

DETAILED DESCRIPTION

The present invention is directed to indane bisphenol monomers of formula (I), as described above. The monomers are commercially valuable monomers for producing a variety of polymers and polymer compositions. Polymers that can be prepared from the monomers of formula (I) include, but are not limited to, homopolymers and copolymers of polycarbonates; polyester-polycarbonates; polyesters; polyesteramides; polyetherimides; polyethers; polyethersulfones; polyepoxides; polycarbonate-polyorganosiloxane block copolymers; copolymers comprising aromatic ester, ester carbonate, and carbonate repeat units; and polyetherketones. Accordingly, the present invention is also directed to polymers comprising structural units derived from the monomers of formula (I), blended compositions comprising the polymers, articles comprising the polymers and blends, methods of using the monomers, polymers, and blends, and processes for preparing the monomers, polymers, and blends.

Polymers comprising structural units derived from monomers of formula (I) may exhibit favorable physical properties (e.g., impact strength, heat resistance, weatherability, ductility, and/or processability), and in particular, compared to polymers derived from other indane bisphenols and/or indanone bisphenols.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

"Alkyl" as used herein may mean a linear, branched, or cyclic hydrocarbyl group, such as a methyl group, ethyl group, n-propyl group, isopropyl group, n-butyl group, isobutyl group, tert-butyl group, n-pentyl group, isopentyl group, n-hexyl group, isohexyl group, cyclopentyl group, cyclohexyl group, and the like.

"Aryl" as used herein may mean a substituted or unsubstituted aryl radical containing from 6 to 36 ring carbon atoms. Examples of aryl include, but are not limited to, a phenyl group, a bicyclic hydrocarbon fused ring system, or a tricyclic hydrocarbon fused ring system wherein one or more of the rings are a phenyl group.

"Arylalkyl" as used herein may mean an aryl, as defined herein, appended to the parent molecular moiety through an alkyl, as defined herein.

"Copolymer" as used herein may mean a polymer derived from two or more structural unit or monomeric species, as opposed to a homopolymer, which is derived from only one structural unit or monomer.

"$C_3$-$C_6$ cycloalkyl" as used herein may mean cyclopropyl, cyclobutyl, cyclopentyl or cyclohexyl.

"Glass Transition Temperature" or "Tg" as used herein may mean the maximum temperature that a polymer, such as a polycarbonate, will have one or more useful properties. These properties include impact resistance, stiffness, strength, and shape retention. The Tg of a polycarbonate therefore may be an indicator of its useful upper temperature limit, particularly in plastics applications. The Tg may be measured using a differential scanning calorimetry method and expressed in degrees Celsius.

The glass transition temperature of a polymer, such as a polycarbonate, may depend primarily on the composition of the polymer. Polycarbonates that are formed from monomers having more rigid and less flexible chemical structures than Bisphenol-A generally have higher glass transition temperatures than Bisphenol-A polycarbonate, while polycarbonates that are formed from monomers having less rigid and more flexible chemical structures than Bisphenol-A generally have lower glass transition temperatures than Bisphenol-A polycarbonate. For example, a polycarbonate described herein formed from 33 mole % of a rigid monomer, 3,3-bis(4-hydroxyphenyl)-2-phenylisoindolin-1-one ("PPPBP"), and 67 mole % Bisphenol-A has a glass transition temperature of 198° C., while a polycarbonate described herein formed from Bisphenol-A, but also having 6 wt % of siloxane units, a flexible monomer, has a glass transition temperature of 145° C.

Mixing of two or more polycarbonates having different glass transition temperatures may result in a glass transition temperature value for the mixture that is intermediate between the glass transition temperatures of the polycarbonates that are mixed.

The glass transition temperature of a polycarbonate may also be an indicator of the molding or extrusion temperatures required to form polycarbonate parts. The higher the glass transition temperature of the polycarbonate the higher the molding or extrusion temperatures that are needed to form polycarbonate parts.

The glass transition temperatures (Tg) described herein are measures of heat resistance of, for example, polycarbonate and polycarbonate blends. The Tg can be determined by differential scanning calorimetry. The calorimetry method may use a TA Instruments Q1000 instrument, for example, with setting of 20° C./min ramp rate and 40° C. start temperature and 200° C. end temperature "Halo" as used herein may be a substituent to which the prefix is attached is substituted with one or more independently selected halogen radicals. For example, "$C_1$-$C_6$ haloalkyl" means a $C_1$-$C_6$ alkyl substituent wherein one or more hydrogen atoms are replaced with independently selected halogen radicals. Non-limiting examples of $C_1$-$C_6$ haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

"Halogen" or "halogen atom" as used herein may mean a fluorine, chlorine, bromine or iodine atom.

"Haze" as used herein may mean that percentage of transmitted light, which in passing through a specimen deviates from the incident beam by forward scattering. Percent (%) haze may be measured according to ASTM D 1003-07.

"Heteroaryl" as used herein may mean any aromatic heterocyclic ring which may comprise an optionally benzocondensed 5 or 6 membered heterocycle with from 1 to 3 heteroatoms selected among N, O or S, Non limiting examples of heteroaryl groups may include pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazotyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

"Hindered phenol stabilizer" as used herein may mean 3,5-di-tert-butyl-4-hydroxyhydrocinnamic acid, octadecyl ester.

"Melt Volume Rate" (MVR) as used herein may mean the flow rate of a polymer in a melt phase as determined using the method of ASTM 1238-10. The MVR of a molten polymer is measured by determining the amount of polymer that flows through a capillary of a specific temperature over a specified time using standard weights at a fixed temperature. MVR is expressed in cubic centimeter per 10 minutes. The higher the MVR value of a polymer at a specific temperature, the greater the flow of that polymer at that specific temperature.

"Percent transmission" or "% transmission" as used herein may mean the ratio of transmitted light to incident light and may be measured according to ASTM D 1003-07.

"PETS release agent" as used herein may mean pentaerythritol tetrastearate, mold release.

"Phosphite stabilizer" as used herein may mean tris-(2,4-di-tert-butylphenyl) phosphite.

"Polycarbonate" as used herein may mean an oligomer or polymer comprising residues of one or more polymer structural units, or monomers, joined by carbonate linkages.

"Straight or branched $C_1$-$C_3$ alkyl" or "straight or branched $C_1$-$C_3$ alkoxy" as used herein may mean methyl, ethyl, n-propyl, isopropyl, methoxy, ethoxy, n-propoxy and isopropoxy.

Unless otherwise indicated, each of the foregoing groups may be unsubstituted or substituted, provided that the substitution does not significantly adversely affect synthesis, stability, or use of the compound.

The terms "structural unit" and "monomer" are interchangeable as used herein.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. MONOMERS

Monomers disclosed herein include indane bisphenol monomers of formula (I),

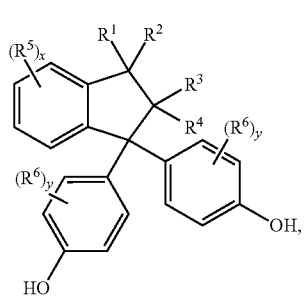

(I)

wherein $R^1$, $R^2$, $R^3$, $R^4$, $R^5$, $R^6$, x, and y are as described in the Summary of the Invention.

In certain embodiments, $R^1$ and $R^2$ are each independently a $C_1$-$C_6$ alkyl. In a preferred embodiment, $R^1$ is methyl and $R^2$ is methyl. In another preferred embodiment, $R^1$ is methyl, $R^2$ is methyl, $R^3$ is hydrogen, and $R^4$ is hydrogen. In another preferred embodiment, $R^1$ is methyl, $R^2$ is methyl, $R^3$ is hydrogen, $R^4$ is hydrogen, x is zero, and y is zero.

In certain embodiments, $R^1$ and $R^2$ are each independently hydrogen or a $C_1$-$C_6$ alkyl. In a preferred embodiment, one of $R^1$ and $R^2$ is a $C_1$-$C_6$ alkyl and the other group is hydrogen. In another preferred embodiment, one of $R^1$ and $R^2$ is methyl and the other group is hydrogen. In another preferred embodiment, one of $R^1$ and $R^2$ is methyl and the other group is hydrogen, $R^3$ is hydrogen, $R^4$ is hydrogen, x is zero, and y is zero.

In certain embodiments, $R^1$, $R^2$, $R^3$, and $R^4$ are each independently a $C_1$-$C_6$ alkyl. In a preferred embodiment, $R^1$ is methyl, $R^2$ is methyl, $R^3$ is methyl, and $R^4$ is methyl. In another preferred embodiment, $R^1$ is methyl, $R^2$ is methyl, $R^3$ is methyl, $R^4$ is methyl, x is zero, and y is zero.

In certain embodiments, at least one of $R^1$ and $R^2$ is other than hydrogen. In certain embodiments, both of $R^1$ and $R^2$ are other than hydrogen.

Exemplary monomer units of formula (I) include, but are not limited to:
4,4'-(3,3-dimethyl-2,2-dihydro-1H-indene-1,1-diyl)diphenol;
4,4'-(3-methyl-2,2,3-trihydro-1H-indene-1,1-diyl)diphenol;
4,4'-(2,3,3-trimethyl-2-hydro-1H-indene-1,1-diyl)diphenol; and
4,4'-(2,2,3,3-tetramethyl-1H-indene-1,1-diyl)diphenol.

The monomers of formula (I) can contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

3. METHOD OF MAKING THE MONOMERS

The monomers disclosed herein can be prepared according to the following synthetic schemes and methods, which illustrate a means by which the monomers can be prepared.

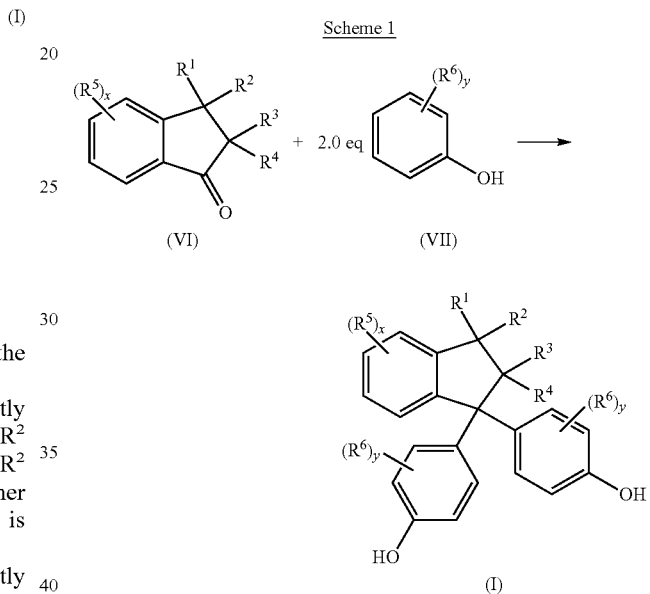

Monomers of formula (I) can be prepared as described in Scheme 1, wherein $R^1$, $R^2$, $R^3$, $R^4$, $R^5$, $R^6$, x, and y, are as defined in the Summary of the Invention. Treating an indanone of formula (VI) with at least two equivalents of a phenol of formula (VII) in the presence of an acid catalyst (e.g., HCl, HBr, HI, BF$_3$, HF, H$_2$SO$_4$, CH$_3$SO$_3$H, CF$_3$CO$_2$H) will provide a monomer of formula (I). Preferably, the reaction is conducted in the presence of a thiol promoter, such as 3-mercaptopropionic acid. In a preferred embodiment, the reaction is conducted in the presence of 3-mercaptopropionic acid ("3-MPA") and sulfuric acid ("H$_2$SO$_4$"). The reaction mixture may be prepared by charging a flask with an indanone of formula (VI), a phenol of formula (VII), and 3-MPA. Sulfuric acid may be slowly added, preferably dropwise, while maintaining the reaction at a temperature of about 25° C. to about 40° C., preferably about 30° C. to about 35° C. After complete addition of the sulfuric acid, the reaction temperature may be raised, preferably to about 45° C. to about 65° C., more preferably to about 55° C., and stirred for a time sufficient (e.g., 14 hours) to provide a monomer of formula (I). The monomer may be isolated and purified by techniques known to the skilled artisan (e.g., extraction, precipitation, recrystallization).

Scheme 2

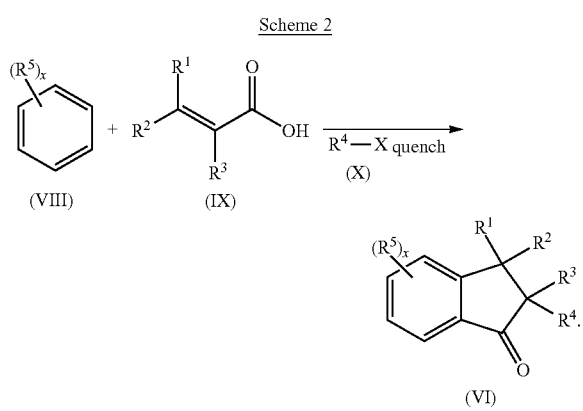

Indanones of formula (VI) can be prepared as described in Scheme 2, wherein $R^1$, $R^2$, $R^3$, $R^4$, $R^5$, and x, are as defined in the Summary of the Invention. Treating a compound of formula (VIII) with an α,β-unsaturated carboxylic acid of formula (IX) in the presence of a Lewis acid catalyst (e.g., anhydrous aluminum chloride ($AlCl_3$), iron(III)chloride ($FeCl_3$)), followed by quenching with a compound of formula (X), wherein X of $R^4$—X is a leaving group or counterion (e.g., halide), will provide indanones of formula (VI). The reaction mixture may be prepared by cooling a solution of a compound of formula (VIII) and a compound of formula (IX) to a temperature of about −10° C. to about 10° C., preferably about 0° C., and thereafter slowly adding a Lewis acid catalyst, such as anhydrous aluminum chloride. The reaction mixture may then be refluxed for a time sufficient (e.g., 7-8 hours) to provide an indanone of formula (VI).

Phenols of formula (VII) are commercially available, and may be purchased from, for example, Sigma-Aldrich (Milwaukee, Wis.). Alternatively, phenols of formula (VII) can be prepared by methods known to those skilled in the art.

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

4. POLYMERS

Polymers disclosed herein include polymers comprising repeating units derived from monomers of formula (I). Polymers that can be prepared from the monomers of formula (I) include, but are not limited to, polycarbonates; polyesterpolycarbonates; polyesters; polyesteramides; polyetherimides; polyethers; polyethersulfones; polyepoxides; polycarbonate-polyorganosiloxane block copolymers; copolymers comprising aromatic ester, ester carbonate, and carbonate repeat units; polyetherketones; and any combination thereof.

The polymers may comprise identical or different repeating units derived from one or more monomers of formula (I). The polymers may comprise one or more repeating units derived from one or more other monomer compounds ("other monomers") (e.g. a second, third, fourth, fifth, sixth, etc., other monomer compound).

The monomers of formula (I) and other monomers may be randomly incorporated into a polymer. For example, a copolymer may be arranged in an alternating sequence following a statistical distribution, which is independent of the mole ratio of the structural units present in the polymer chain. A random copolymer may have a structure, which can be indicated by the presence of several block sequences (I—I) of monomers of formula (I) and other monomers (O—O) and alternate sequences (I—O) or (O—I), that follow a statistical distribution. In a random x:(1-x) copolymer, wherein x is the mole percent of the other monomer(s) and 1-x is the mole percent of the monomer of formula (I), one can calculate the distribution of each monomer using peak area values determined by $^{13}C$ NMR, for example.

A copolymer may have alternating copolymers with regular alternating I and O units (—I—O—I—O—I—O—I—O—), or I and O units arranged in a repeating sequence (e.g. a periodic copolymer having the formula: (I—O—I—O—O—I—I—I—I—O—O—O)n). The copolymer may be a statistical copolymer in which the sequence of monomer residues follows a statistical rule. For example, if the probability of finding a given type monomer residue at a particular point in the chain is equal to the mole fraction of that monomer residue in the chain, then the polymer may be referred to as a truly random copolymer. The copolymer may be a block copolymer that comprises two or more homopolymer subunits linked by covalent bonds (—I—I—I—I—I—O—O—O—O—O—). The union of the homopolymer subunits may require an intermediate non-repeating subunit, known as a junction block. Block copolymers with two or three distinct blocks are called diblock copolymers and triblock copolymers, respectively.

Polymers comprising repeating units derived from monomers of formula (I) may include any suitable mole % of units derived from monomers of formula (I). The polymers may comprise about 1% to about 100%, about 5% to about 95%, about 10% to about 90%, about 15% to about 85%, about 20% to about 80%, about 25% to about 75%, about 30% to about 70%, about 35% to about 65%, about 40% to about 60%, or about 45% to about 55% mole % monomer of formula (I). In certain embodiments, the polymers comprise about 30% to about 100% mole % of monomer of formula (I). In certain embodiments, the polymers comprise 10%, 15%, 20%, 25%, 30%, 35%, 40%, 45%, 50%, 55%, 60%, 65%, 70%, 75%, 80%, 85%, 90%, 95%, or 100% mole % of monomer of formula (I). In certain embodiments, the polymers comprise about 32%, about 45%, about 55%, about 65%, or about 100% mole % of monomer of formula (I).

(A) Polycarbonates

The polymers disclosed herein include polycarbonates comprising repeating units derived from monomers of formula (I). The polycarbonates include homopolycarbonates, copolymers comprising different moieties in the carbonate (referred as "copolycarbonates"), copolymers comprising carbonate units and other types of polymer units such as polyester units, polysiloxane units, and combinations comprising at least one homopolycarbonate and copolycarbonate.

Polycarbonates comprising repeating units derived from monomers of formula (I) may be particularly useful for high heat applications. Accordingly, the polycarbonates may have a glass transition temperature (Tg) of greater than 150° C., 155° C., 160° C., 165° C., 170° C., 175° C., 180° C., 185° C., 190° C., 200° C., 210° C., 220° C., 230° C., 240° C., 250° C., 260° C., 270° C., 280° C., 290° C., or 300° C., as measured using a differential scanning calorimetry method. In certain embodiments, the polycarbonates have glass transition temperatures ranging from about 150° C. to about 230° C., or about 170° C. to about 220° C. In certain embodiments, the polycarbonates have glass transition temperatures of about 170° C., about 180° C., about 185° C., about 190° C., or about 210° C. In certain embodiments, the polycarbonates have glass transition temperatures of 168.1° C., 179.83° C., 182.2° C., 186.9° C., 189.8° C., or 209° C. The polycarbonates may exhibit a heat resistance higher than the levels achieved with bisphenol-A (BPA) homopolymer. In one embodiment, the polycarbonate must have a glass transition temperature of greater than 170° C.

Polycarbonates comprising repeating units derived from monomers of formula (I) may have a weight average molecular weight (Mw) of about 1,500 to about 150,000 g/mol [$\pm$1,000 g/mol], of about 10,000 to about 125,000 g/mol [$\pm$1,000 g/mol], of about 50,000 to about 100,000 g/mol [$\pm$1,000 g/mol], or of about 75,000 to about 90,000 g/mol [$\pm$1,000 g/mol]. In certain embodiments, the polycarbonates have a weight average molecular weight of about 5,000 to about 50,000 g/mol [$\pm$1,000 g/mol], about 10,000 to about 30,000 g/mol [$\pm$1,000 g/mol], about 15,000 to about 25,000 g/mol [$\pm$1,000 g/mol], or about 17,000 to about 23,000 g/mol [$\pm$1,000 g/mol]. In certain embodiments, the polycarbonates have weight average molecular weights of about 17,000 g/mol [$\pm$1,000 g/mol], about 18,000 g/mol [$\pm$1,000 g/mol], about 19,000 g/mol [$\pm$1,000 g/mol], about 20,000 g/mol [$\pm$1,000 g/mol], about 21,000 g/mol [$\pm$1,000 g/mol], about 22,000 g/mol [$\pm$1,000 g/mol], or about 23,000 g/mol [$\pm$1,000 g/mol]. In certain embodiments, the polycarbonates have weight average molecular weights of 17,087, 17,466, 18,780, 19,964, 20,140, 20,318, 20,533, 21,029, 22,477, 23,303, or 23,413. Molecular weight determinations may be performed using gel permeation chromatography (GPC), using a crosslinked styrene-divinylbenzene column and calibrated to polycarbonate references. Samples may be prepared at a concentration of about 1 mg/ml, and eluted at a flow rate of about 1.0 ml/min.

Polycarbonates comprising repeating units derived from monomers of formula (I) may have a polydispersity index (PDI) of about 1.0 to about 10.0, about 2.0 to about 7.0, or about 2.5 to about 5.0. In certain embodiments, the polycarbonates have PDIs of about 2.50, about 3.00, about 3.50, about 4.00, about 4.50, or about 5.00. In certain embodiments, the polycarbonates have PDIs of 2.64, 2.70, 2.83, 2.99, 3.02, 3.29, 3.40, 3.48, 3.77, 4.80, or 4.92.

Polycarbonates comprising repeating units derived from monomers of formula (I) may have a melt volume flow rate (often abbreviated MVR), which measures the rate of extrusion of a composition through an orifice at a prescribed temperature and load. In certain embodiments, the polycarbonates may have an MVR of 2 to 70, specifically 4 to 60, using the ASTM D1238 method, 2.16 kg load, 330° C. temperature, 360 second dwell.

Polycarbonates comprising repeating units derived from monomers of formula (I) may have a biocontent of 2 weight % to 90 weight %; 5 weight % to 25 weight %; 10 weight % to 30 weight %; 15 weight % to 35 weight %; 20 weight % to 40 weight %; 25 weight % to 45 weight %; 30 weight % to 50 weight %; 35 weight % to 55 weight %; 40 weight % to 60 weight %; 45 weight % to 65 weight %; 55 weight % to 70% weight %; 60 weight % to 75 weight %; 50 weight % to 80 weight %; or 50 weight % to 90 weight %. The biocontent may be measured according to ASTM D6866.

(i) Homopolycarbonates

The polycarbonate may be a homopolycarbonate derived from monomers of formula (I). The homopolycarbonate may include repeating structural units of formula (I):

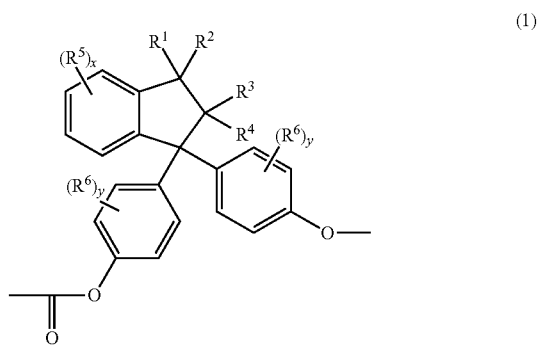

wherein $R^1$, $R^2$, $R^3$, $R^4$, $R^5$, $R^6$, x, and y, are as defined in the Summary of the Invention.

In certain embodiments, $R^1$ and $R^2$ are each independently a $C_1$-$C_6$ alkyl. In a preferred embodiment, $R^1$ is methyl and $R^2$ is methyl. In another preferred embodiment, $R^1$ is methyl, $R^2$ is methyl, $R^3$ is hydrogen, and $R^4$ is hydrogen. In another preferred embodiment, $R^1$ is methyl, $R^2$ is methyl, $R^3$ is hydrogen, $R^4$ is hydrogen, x is zero, and y is zero.

In certain embodiments, $R^1$ and $R^2$ are each independently hydrogen or a $C_1$-$C_6$ alkyl. In a preferred embodiment, one of $R^1$ and $R^2$ is $C_1$-$C_6$ alkyl and the other group is hydrogen. In another preferred embodiment, one of $R^1$ and $R^2$ is methyl and the other group is hydrogen. In another preferred embodiment, one of $R^1$ and $R^2$ is methyl and the other group is hydrogen, $R^3$ is hydrogen, $R^4$ is hydrogen, x is zero, and y is zero.

In certain embodiments, $R^1$, $R^2$, $R^3$, and $R^4$ are each independently a $C_1$-$C_6$ alkyl. In a preferred embodiment, $R^1$ is methyl, $R^2$ is methyl, $R^3$ is methyl, and $R^4$ is methyl. In another preferred embodiment, $R^1$ is methyl, $R^2$ is methyl, $R^3$ is methyl, $R^4$ is methyl, x is zero, and y is zero.

(ii) Copolycarbonates

The polycarbonate may be a copolycarbonate including repeating units of formula (1), as described above, and at least one repeating unit (a second repeating unit) that is different from the repeating unit of formula (1). The second repeating unit may have formula (2):

wherein $R^{100}$ may comprise any suitable organic group, such as an aliphatic, alicyclic, or aromatic group, or any combination thereof. In certain embodiments, $R^{100}$ in the carbonate units of formula (2) may be a $C_6$-$C_{36}$ aromatic group wherein at least one moiety is aromatic. In certain embodiments, $R^{100}$ may be derived from monomer units of formula (I). In other embodiments, $R^{100}$ may be derived from monomer units other than the monomer units of formula (I).

In certain embodiments, each $R^{100}$ may be an aromatic organic group, for example, a group of formula (3):

wherein each of the $A^1$ and $A^2$ is a monocyclic divalent aryl group and $Y^1$ is a bridging group having one or two atoms that separate $A^1$ and $A^2$. For example, one atom may separate $A^1$ from $A^2$, with illustrative examples of these groups including —O—, —S—, —S(O)—, —S(O)$_2$—, —C(O)—, methylene, cyclohexyl-methylene, 2-[2.2.1]-bicycloheptylidene, ethylidene, isopropylidene, neopentylidene, cyclohexylidene, cyclopentadecyclidene, cyclododecylidene, and adamantylidene. The bridging group of $Y^1$ may be a hydrocarbon group or a saturated hydrocarbon group such as methylene, cyclohexylidene, or isopropylidene.

Each $R^{100}$ may be derived from a dihydroxy monomer unit. The dihydroxy monomer unit may have formula (4):

$$HO-A^1-Y^1-A^2-OH \quad (4)$$

wherein each of the $A^1$ and $A^2$ is a monocyclic divalent aryl group and $Y^1$ is a bridging group having one or two atoms that separate $A^1$ and $A^2$. For example, one atom may separate $A^1$ from $A^2$, with illustrative examples of these groups including —O—, —S—, —S(O)—, —S(O)$_2$—, —C(O)—, methylene, cyclohexyl-methylene, 2-[2.2.1]-bicycloheptylidene, ethylidene, isopropylidene, neopentylidene, cyclohexylidene, cyclopentadecyclidene, cyclododecylidene, and adamantylidene. The bridging group of $Y^1$ may be a hydrocarbon group or a saturated hydrocarbon group such as methylene, cyclohexylidene, or isopropylidene.

The dihydroxy monomer unit of formula (4) may include bisphenol compounds of the general formula (5):

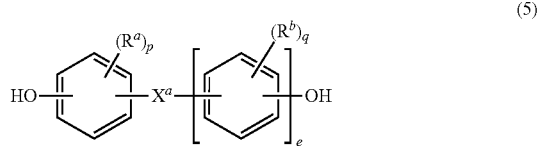

wherein $X^a$ may be a bridging group connecting the two hydroxy-substituted aromatic groups, where the bridging group and the hydroxy substituent of each $C_6$ arylene group are disposed ortho, meta, or para (specifically para) to each other on the $C_6$ arylene group. For example, the bridging group $X^a$ may be single bond, —O—, —S—, —C(O)—, or a $C_1$-$C_{18}$ organic group. The $C_1$-$C_{18}$ organic bridging group may be cyclic or acyclic, aromatic or non-aromatic, and can further comprise heteroatoms such as halogens, oxygen, nitrogen, sulfur, silicon, or phosphorous. The $C_1$-$C_{18}$ organic group can be disposed such that the $C_6$ arylene groups connected thereto are each connected to a common alkylidene carbon or to different carbons of the $C_1$-$C_{18}$ organic bridging group. $R^a$ and $R^b$ may each represent a halogen, $C_1$-$C_{12}$ alkyl group or combination thereof. For example, $R^a$ and $R^b$ may each be a $C_1$-$C_3$ alkyl group, specifically methyl, disposed meta to the hydroxy group on each arylene group. The designation (e) is 0 or 1. The numbers p and q are each independently integers of 0 to 4. It will be understood that $R^a$ is hydrogen when p is 0, and likewise $R^b$ is hydrogen when q is 0.

In certain embodiments, $X^a$ may be substituted or unsubstituted $C_3$-$C_{18}$ cycloalkylidene, a $C_1$-$C_{25}$ alkylidene of formula —C($R^c$)($R^d$)— wherein $R^c$ and $R^d$ are each independently hydrogen, $C_1$-$C_{12}$ alkyl, $C_1$-$C_{12}$ cycloalkyl, $C_7$-$C_{12}$ arylalkyl, $C_1$-$C_{12}$ heteroalkyl, or cyclic $C_7$-$C_{12}$ heteroarylalkyl, or a group of the formula —C(=$R^e$)— wherein $R^e$ is a divalent $C_1$-$C_{12}$ hydrocarbon group. This may include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene. A specific example wherein $X^a$ is a substituted cycloalkylidene is the cyclohexylidene-bridged, alkyl-substituted bisphenol of formula (6):

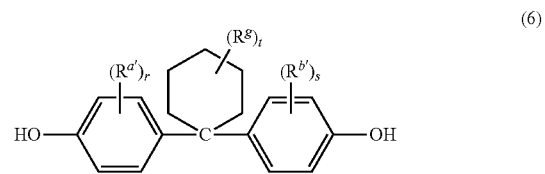

wherein $R^{a'}$ and $R^{b'}$ are each independently $C_1$-$C_{12}$ alkyl, $R^g$ is $C_1$-$C_{12}$ alkyl or halogen, r and s are each independently 1 to 4, and t is 0 to 10. $R^{a'}$ and $R^{b'}$ may be disposed meta to the cyclohexylidene bridging group. The substituents $R^{a'}$, $R^{b'}$ and $R^g$ may, when comprising an appropriate number of carbon atoms, be straight chain, cyclic, bicyclic, branched, saturated, or unsaturated. For example, $R^{a'}$, $R^{b'}$ and $R^g$ may be each independently $C_1$-$C_4$ alkyl, r and s are each 1, and t is 0 to 5. In another example, $R^{a'}$, $R^{b'}$ and $R^g$ may each be methyl, r and s are each 1, and t is 0 or 3. The cyclohexylidene-bridged bisphenol can be the reaction product of two moles of o-cresol with one mole of cyclohexanone. In another example, the cyclohexylidene-bridged bisphenol may be the reaction product of two moles of a cresol with one mole of a hydrogenated isophorone (e.g., 1,1,3-trimethyl-3-cyclohexane-5-one). Such cyclohexane-containing bisphenols, for example the reaction product of two moles of a phenol with one mole of a hydrogenated isophorone, are useful for making polycarbonate polymers with high glass transition temperatures and high heat distortion temperatures. Cyclohexyl bisphenol-containing polycarbonates, or a combination comprising at least one of the foregoing with other bisphenol polycarbonates, are supplied by Bayer Co. under the APEC® trade name.

$X^a$ may be a $C_1$-$C_{18}$ alkylene group, a $C_3$-$C_{18}$ cycloalkylene group, a fused $C_6$-$C_{18}$ cycloalkylene group, or a group of the formula —$B^1$—W—$B^2$— wherein $B^1$ and $B^2$ are the same or different $C_1$-$C_6$ alkylene group and W is a $C_3$-$C_{12}$ cycloalkylidene group or a $C_6$-$C_{16}$ arylene group.

In another example, $X^a$ may be a substituted $C_3$-$C_{18}$ cycloalkylidene of the formula (7):

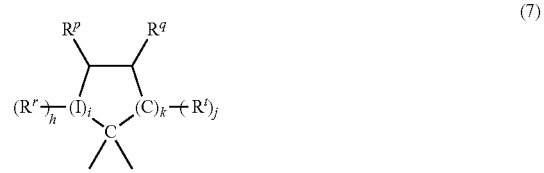

wherein $R^r$, $R^p$, $R^q$ and $R^t$ are each independently hydrogen, halogen, oxygen, or $C_1$-$C_{12}$ organic groups; I is a direct bond, a carbon, or a divalent oxygen, sulfur, or —N(Z)— where Z is hydrogen, halogen, hydroxy, $C_1$-$C_{12}$ alkyl, $C_1$-$C_{12}$ alkoxy, $C_6$-$C_{12}$ aryl, or $C_1$-$C_{12}$ acyl; h is 0 to 2, j is 1 or 2, is an integer of 0 or 1, and k is an integer of 0 to 3, with the proviso that at least two of $R^r$, RP, $R^q$ and $R^t$ taken together are a fused cycloaliphatic, aromatic, or heteroaromatic ring. It will be understood that where the fused ring is aromatic, the ring as shown in formula (7) will have an unsaturated carbon-carbon linkage where the ring is fused. When i is 0, h is 0, and k is 1, the ring as shown in formula (7) contains 4 carbon atoms; when i is 0, h is 0, and k is 2, the ring as shown contains 5 carbon atoms, and when i is 0, h is 0, and k is 3, the ring contains 6 carbon atoms. In one example, two adjacent groups (e.g., $R^q$ and $R^t$ taken together) form an aromatic group, and in another embodiment, $R^q$ and $R^t$ taken together form one aromatic group and $R^r$ and $R^p$ taken together form a second aromatic group. When $R^q$ and $R^r$ taken together form an aromatic group, $R^p$ can be a double-bonded oxygen atom, i.e., a ketone.

Other useful dihydroxy monomer units include aromatic dihydroxy compounds of formula (8):

(8)

wherein each $R^h$ is independently a halogen atom, a $C_1$-$C_{10}$ hydrocarbyl such as a $C_1$-$C_{10}$ alkyl group, a halogen substituted $C_1$-$C_{10}$ hydrocarbyl such as a halogen-substituted $C_1$-$C_{10}$ alkyl group, and n is 0 to 4. The halogen, when present, is usually bromine.

Bisphenol-type dihydroxy aromatic compounds may include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxy-3-methylphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, (alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorene, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as combinations comprising at least one of the foregoing dihydroxy aromatic compounds.

Examples of the types of bisphenol compounds represented by formula (4) may include 1,1-bis(4-hydroxyphenyl) methane, 1,1-bis(4-hydroxyphenyl)ethane, 2,2-bis(4-hydroxyphenyl)propane (also referred to as "bisphenol-A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, 1,1-bis(4-hydroxy-t-butylphenyl) propane, 3,3-bis(4-hydroxyphenyl)phthalimidine, 2-phenyl-3,3-bis(4-hydroxyphenyl)phthalimidine ("PPPBP"), 9,9-bis(4-hydroxyphenyl)fluorene, and 1,1-bis(4-hydroxy-3-methylphenyl)cyclohexane ("DMBPC"). Combinations comprising at least one of the foregoing dihydroxy aromatic compounds can also be used.

The dihydroxy compounds of formula (4) may be the following formula (9) for high heat applications:

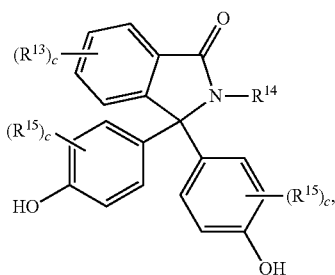

(9)

wherein $R^{13}$ and $R^{15}$ are each independently a halogen or a $C_1$-$C_6$ alkyl group, $R^{14}$ is a $C_1$-$C_6$ alkyl, phenyl, or phenyl substituted with up to five halogens or $C_1$-$C_6$ alkyl groups, and c is 0 to 4. In a specific embodiment, $R^{14}$ is a $C_1$-$C_6$ alkyl or phenyl group. In still another embodiment, $R^{14}$ is a methyl or phenyl group. In another specific embodiment, each c is 0.

The dihydroxy compounds of formula (4) may be the following formula (10) for high heat applications:

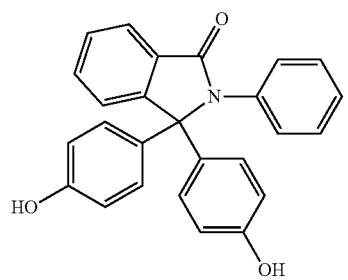

(10)

(also known as 3,3-bis(4-hydroxyphenyl)-2-phenylisoindolin-1-one (PPPBP)).

Alternatively, the dihydroxy compounds of formula (4) may be the following formula (11) for high heat applications:

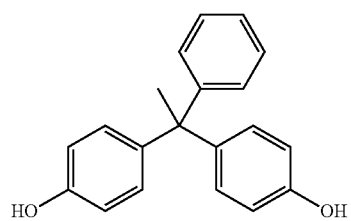

(11)

(also known as 4,4'-(1-phenylethane-1,1-diyl)diphenol (bisphenol-AP) or 1,1-bis(4-hydroxyphenyl)-1-phenylethane).

Alternatively, the dihydroxy compounds of formula (4) may be the following formula (12) for high heat applications:

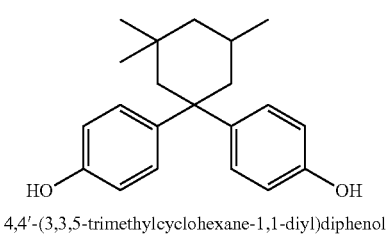

4,4'-(3,3,5-trimethylcyclohexane-1,1-diyl)diphenol (bisphenol TMC) or 1,1-bis(4-hydroxyphenyl)-3,3,5-trimethylcyclohexane).

Other dihydroxy compounds that might impart high Tgs to the polycarbonate as a copolycarbonate are dihydroxy compounds having adamantane units, as described in U.S. Pat. No. 7,112,644 and U.S. Pat. No. 3,516,968, which are fully incorporated herein by reference. A compound having adamantane units may have repetitive units of the following formula (13) for high heat applications:

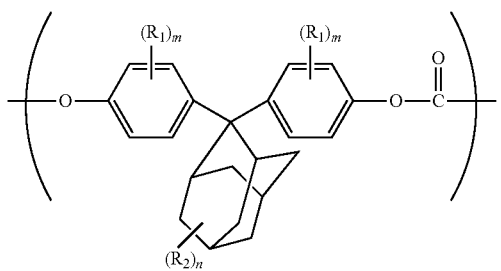

wherein $R_1$ represents a halogen atom, an alkyl group having 1 to 6 carbon atoms, an alkoxy group having 1 to 6 carbon atoms, an aryl group having 6 to 12 carbon atoms, an aryl-substituted alkenyl group having 7 to 13 carbon atoms, or a fluoroalkyl group having 1 to 6 carbon atoms; $R_2$ represents a halogen atom, an alkyl group having 1 to 12 carbon atoms, an alkoxy group having 1 to 12 carbon atoms, an aryl group having 6 to 12 carbon atoms, an aryl-substituted alkenyl group having 7 to 13 carbon atoms, or a fluoroalkyl group having 1 to 12 carbon atoms; m represents an integer of 0 to 4; and n represents an integer of 0 to 14.

Other dihydroxy compounds that might impart high Tgs to the polycarbonate as a copolycarbonate are dihydroxy compounds having fluorene-units, as described in U.S. Pat. No. 7,244,804. One such fluorene-unit containing dihydroxy compound is represented by the following formula (14) for high heat applications:

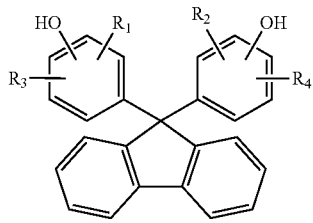

wherein $R_1$ to $R_4$ are each independently a hydrogen atom, a hydrocarbon group with 1 to 9 carbon atoms which may contain an aromatic group, or a halogen atom.

(iii) Isosorbide-Containing Polycarbonates

The polycarbonate may be a copolymer comprising repeating units of formula (1) as described above, and other types of polymer units such isosorbide containing polycarbonate units. In certain embodiments, $R^{100}$ of formula (2) may be derived from a monomer unit derived from isosorbide. Optionally, the polycarbonate may comprise repeating units derived from monomers of formula (I), repeating units derived from monomers of formula (4), and repeating units derived from a monomer unit derived from isosorbide. The monomer unit derived from isosorbide may be an isorbide-bisphenol unit of formula (15):

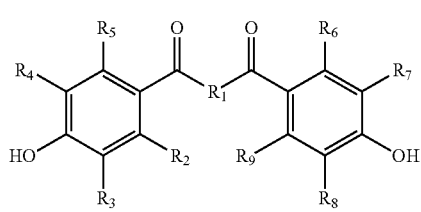

wherein $R_1$ is an isosorbide unit and $R_2$-$R_9$ are each independently a hydrogen, a halogen, a $C_1$-$C_6$ alkyl, a methoxy, an ethoxy, or an alkyl ester.

The $R_1$ isosorbide unit may be represented by formula (16):

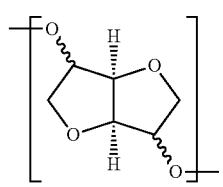

The isosorbide unit may be derived from an isosorbide, a mixture of isosorbide, a mixture of isomers of isosorbide, and/or from individual isomers of isosorbide. The stereochemistry for the isosorbide-based carbonate units of formula (16) is not particularly limited.

The $R_1$ isosorbide unit may be derived from an isosorbide of general formula (17):

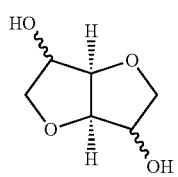

and can be a single diol isomer or mixture of diol isomers. The stereochemistry for the isosorbide of formula (17) is also not particularly limited. These diols may be prepared by the dehydration of the corresponding hexitols. Hexitols are produced commercially from the corresponding sugars (aldohexose). Aliphatic diols of formula (17) include 1,4:3,6-dianhydro-D glucitol, of formula (18); 1,4:3,6-dianhydro-D mannitol, of formula (19); and 1,4:3,6-dianhydro-L iditol, of formula (20), and any combination thereof. Isosorbides are available commercially from various chemical suppliers including Cargill, Roquette, and Shanxi.

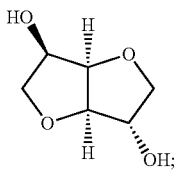
(18)

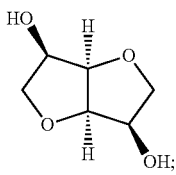
(19)

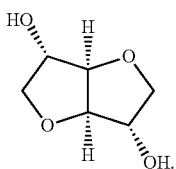
(20)

The diol of formula (17) may be desirable because it is a rigid, chemically and thermally stable aliphatic diol that may be used to produce higher Tg copolymers. The isosorbide-bisphenol may have a pKa of between 8 and 11.

(iv) Polyester-Polycarbonates

The polycarbonate may be a copolymer comprising repeating units of formula (1) as described above, and other types of polymer units such as polyester units. A specific type of copolymer may be a polyester-polycarbonate. The polyester-polycarbonate may comprise repeating units of formula (1), as described above, and repeating ester units of formula (21a):

(21a)

wherein O-D-O of formula (21a) is a divalent group derived from a dihydroxy compound, and D may be, for example, one or more alkyl containing $C_6$-$C_{20}$ aromatic group(s), or one or more $C_6$-$C_{20}$ aromatic group(s), a $C_2$-$C_{10}$ alkylene group, a $C_6$-$C_{20}$ alicyclic group, a $C_6$-$C_{20}$ aromatic group or a polyoxyalkylene group in which the alkylene groups contain 2 to about 6 carbon atoms, specifically 2, 3, or 4 carbon atoms. D may be a $C_2$-$C_{30}$ alkylene group having a straight chain, branched chain, or cyclic (including polycyclic) structure. O-D-O may be derived from a monomer of formula (I), as described above. O-D-O may be derived from an aromatic dihydroxy compound of formula (4), as described above. O-D-O may be derived from an aromatic dihydroxy compound of formula (5), as described above. O-D-O may be derived from an aromatic dihydroxy compound of Formula (15), as described above.

Optionally, the polyester-polycarbonate may comprise carbonate repeating units of formula (2), in addition to carbonate repeating units of formula (1). Optionally, the polyester-polycarbonate may comprise carbonate repeating units of formula (2), and polyester repeating units derived from monomers of formula (I) and a diacid. Optionally, the polyester-polycarbonate may comprise carbonate repeating units derived from monomers other than the monomers of formula (I), and the polyester repeating units may be derived from monomers of formula (I).

The molar ratio of ester units to carbonate units in the polyester-polycarbonates may vary broadly, for example 1:99 to 99:1, specifically 10:90 to 90:10, more specifically 25:75 to 75:25, optionally expanded depending on the desired properties of the final composition.

T of formula (21a) may be a divalent group derived from a dicarboxylic acid, and may be, for example, a $C_2$-$C_{10}$ alkylene group, a $C_6$-$C_{20}$ alicyclic group, a $C_6$-$C_{20}$ alkyl aromatic group, a $C_6$-$C_{20}$ aromatic group, or a $C_6$-$C_{36}$ divalent organic group derived from a dihydroxy compound or chemical equivalent thereof. T may be an aliphatic group, wherein the molar ratio of carbonate units to ester units of formula (21a) in the poly(aliphatic ester)-polycarbonate copolymer is from 99:1 to 60:40; and 0.01 to 10 weight percent, based on the total weight of the polymer component, of a polymeric containing compound. T may be derived from a $C_6$-$C_{20}$ linear aliphatic alpha-omega (β-ω) dicarboxylic ester.

Diacids from which the T group in the ester unit of formula (21a) is derived include aliphatic dicarboxylic acids having from 6 to about 36 carbon atoms, optionally from 6 to 20 carbon atoms. The $C_6$-$C_{20}$ linear aliphatic alpha-omega (α-ω) dicarboxylic acids may be adipic acid, sebacic acid, 3,3-dimethyl adipic acid, 3,3,6-trimethyl sebacic acid, 3,3,5,5-tetramethyl sebacic acid, azelaic acid, dodecanedioic acid, dimer acids, cyclohexane dicarboxylic acids, dimethyl cyclohexane dicarboxylic acid, norbornane dicarboxylic acids, adamantane dicarboxylic acids, cyclohexene dicarboxylic acids, or $C_{14}$, $C_{18}$ and $C_{20}$ diacids.

The ester units of the polyester-polycarbonates of formula (21a) can be further described by formula (21b), wherein T is $(CH_2)_m$, where m is 4 to 40.

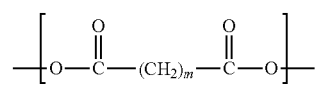
(21b)

Saturated aliphatic alpha-omega dicarboxylic acids may be adipic acid, sebacic or dodecanedioic acid. Sebacic acid is a dicarboxylic acid having the following formula (22):

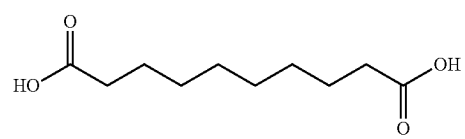
(22)

Sebacic acid has a molecular mass of 202.25 g/mole, a density of 1.209 g/cm$^3$ (25° C.), and a melting point of 294.4° C. at 100 mmHg. Sebacic acid is extracted from castor bean oil found in naturally occurring castor beans.

Other examples of aromatic dicarboxylic acids that may be used to prepare the polyester units include isophthalic or terephthalic acid, 1,2-di(p-carboxyphenyl)ethane, 4,4'-dicarboxydiphenyl ether, 4,4'-bisbenzoic acid, and combinations comprising at least one of the foregoing acids. Acids containing fused rings can also be present, such as in 1,4-, 1,5-, or 2,6-naphthalenedicarboxylic acids. Specific dicarboxylic acids may be terephthalic acid, isophthalic acid, naphthalene dicarboxylic acid, cyclohexane dicarboxylic acid, or combinations thereof. A specific dicarboxylic acid comprises a combination of isophthalic acid and terephthalic acid wherein the weight ratio of isophthalic acid to terephthalic acid is about 91:9 to about 2:98.

D of the repeating units of formula (21a) may also be a $C_2$-$C_6$ alkylene group and T may be p-phenylene, m-phenylene, naphthalene, a divalent cycloaliphatic group, or a combination thereof. This class of polyester includes the poly(alkylene terephthalates).

Mixtures of the diacids can also be employed. It should be noted that although referred to as diacids, any ester precursor could be employed such as acid halides, specifically acid chlorides, and diaromatic esters of the diacid such as diphenyl, for example the diphenyl ester of sebacic acid. With reference to the diacid carbon atom number earlier mentioned, this does not include any carbon atoms which may be included in the ester precursor portion, for example diphenyl. It may be desirable that at least four, five or six carbon bonds separate the acid groups. This may reduce the formation of undesirable and unwanted cyclic species.

The polyester unit of a polyester-polycarbonate may be derived from the reaction of a combination of isophthalic and terephthalic diacids (or derivatives thereof) with resorcinol. In another embodiment, the polyester unit of a polyester-polycarbonate may be derived from the reaction of a combination of isophthalic acid and terephthalic acid with bisphenol-A. In an embodiment, the polycarbonate units may be derived from bisphenol-A. In another specific embodiment, the polycarbonate units may be derived from resorcinol and bisphenol-A in a molar ratio of resorcinol carbonate units to bisphenol-A carbonate units of 1:99 to 99:1.

Useful polyesters may include aromatic polyesters, poly(alkylene esters) including poly(alkylene arylates), and poly(cycloalkylene diesters). Aromatic polyesters may have a polyester structure according to formula (21a), wherein D and T are each aromatic groups as described hereinabove. Useful aromatic polyesters may include, for example, poly(isophthalate-terephthalate-resorcinol) esters, poly(isophthalate-terephthalate-bisphenol-A) esters, poly[(isophthalate-terephthalate-resorcinol) ester-co-(isophthalate-terephthalate-bisphenol-A)]ester, or a combination comprising at least one of these.

The polyester-polycarbonate may have a biocontent according to ASTM-D-6866 of at least 2 weight %, at least 3 weight %, at least 4 weight %, at least 5 weight %, at least 6 weight %, at least 7 weight %, at least 8 weight %, at least 9 weight %, at least 10 weight %, at least 11 weight %, at least 12 weight %, at least 13 weight %, at least 14 weight %, at least 15 weight %, at least 16 weight %, at least 17 weight %, at least 18 weight %, at least 19 weight %, at least 20 weight %, at least 25 weight %, at least 30 weight %, at least 35 weight %, at least 40 weight %, at least 45 weight %, at least 50 weight %, at least 55 weight %, at least 60 weight %, or at least 65 weight % of the composition derived therefrom. The polymer, or any composition derived therefrom, may have at least 5.0 weight percent of sebacic acid content.

(v) Polycarbonate Polysiloxane Copolymers

The polycarbonate may be a copolymer comprising repeating units of formula (1) as described above, and other types of polymer units such as polysiloxane units. The carbonate units of formula (1) may be derived from one or more monomers of formula (I). Optionally, the polycarbonate structural unit of the polycarbonate-polysiloxane copolymer may further comprise carbonate units derived from other monomers, such as the monomers of formula (4), formula (5), and/or formula (15), as described above.

The polysiloxane structural unit may be derived from siloxane-containing dihydroxy compounds (also referred to herein as "hydroxyaryl end-capped polysiloxanes") that contain diorganosiloxane units blocks of formula (23):

(23)

wherein each occurrence of R is the same or different, and is a $C_1$-$C_{13}$ monovalent organic group. For example, R can be a $C_1$-$C_{13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{14}$ aryl group, $C_6$-$C_{10}$ aryloxy group, $C_7$-$C_{13}$ aralkyl group, $C_7$-$C_{13}$ aralkoxy group, $C_7$-$C_{13}$ alkylaryl group, or $C_7$-$C_{13}$ alkylaryloxy group. The foregoing groups can be fully or partially halogenated with fluorine, chlorine, bromine, or iodine, or a combination thereof. In an embodiment, where a transparent polycarbonate is desired, R does not contain any halogen. Combinations of the foregoing R groups can be used in the same polycarbonate.

The value of E in formula (23) can vary widely depending on the type and relative amount of each of the different units in the polycarbonate, the desired properties of the polycarbonate, and like considerations. Generally, E can have an average value of about 2 to about 1,000, specifically about 2 to about 500, more specifically about 2 to about 100. In an embodiment, E has an average value of about 4 to about 90, specifically about 5 to about 80, and more specifically about 10 to about 70. Where E is of a lower value, e.g., less than about 40, it can be desirable to use a relatively larger amount of the units containing the polysiloxane. Conversely, where E is of a higher value, e.g., greater than about 40, it can be desirable to use a relatively lower amount of the units containing the polysiloxane.

In one embodiment, the polysiloxane blocks are provided by repeating structural units of formula (24):

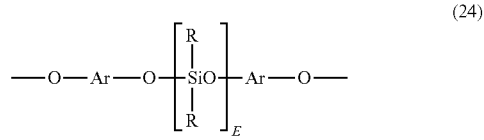

(24)

wherein E is as defined above; each R is the same or different, and is as defined above; and each Ar is the same or different, and Ar is one or more $C_6$-$C_{30}$ aromatic group(s), or one or more alkyl containing $C_6$-$C_{30}$ aromatic group(s), wherein the bonds are directly connected to an aromatic moiety. —O—Ar—O— groups in formula (24) can be, for example, a $C_6$-$C_{30}$ dihydroxyaromatic compound. Combinations comprising at least one of the foregoing dihydroxyaromatic compounds can also be used. Exemplary dihydroxyaromatic compounds are 1,1-bis(4-hydroxyphenyl)methane, 1,1-bis(4-hydroxyphenyl)ethane, 2,2-bis(4-hydroxyphenyl)propane, 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, 1,1-bis(4-hydroxyphenyl)cyclohexane, bis(4-hydroxyphenyl sulfide), 1,1-bis(4-hydroxy-3-methylphenyl)

cyclohexane, and 1,1-bis(4-hydroxy-t-butylphenyl)propane, or a combination comprising at least one of the foregoing dihydroxy compounds.

Polycarbonates comprising such units can be derived from the corresponding dihydroxy compound of formula (25):

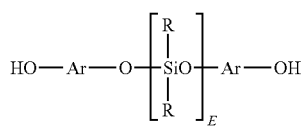
(25)

wherein Ar and E are as described above. Compounds of formula (25) can be obtained by the reaction of a dihydroxyaromatic compound with, for example, an alpha, omega-bis-acetoxy-polydiorganosiloxane oligomer under phase transfer conditions. Compounds of formula (25) can also be obtained from the condensation product of a dihydroxyaromatic compound, with, for example, an alpha, omega bis-chloro-polydimethylsiloxane oligomer in the presence of an acid scavenger.

In a specific embodiment, Ar from formula (25) is derived from resorcinol, and the polydiorganosiloxane repeating units are a dihydroxy aromatic compound of formula (26):

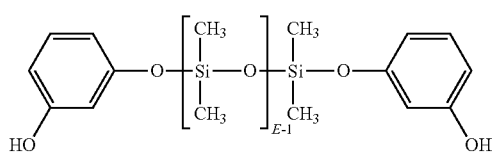
(26)

or, wherein Ar is derived from bisphenol-A, and the polydiorganosiloxane repeating units are a dihydroxy aromatic compound of formula (27):

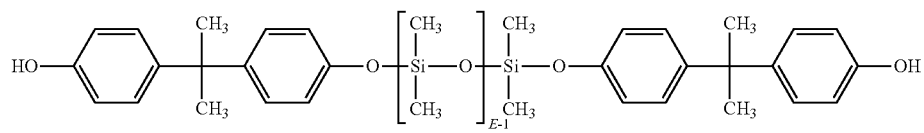
(27)

wherein E has an average value of between 20 and 75.

In another embodiment, polydiorganosiloxane blocks comprise units of formula (28):

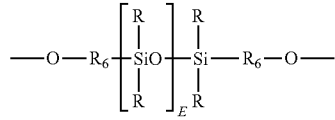
(28)

wherein R and E are as described above, and each $R_6$ is independently a divalent $C_1$-$C_{30}$ organic group such as a $C_1$-$C_{30}$ alkyl, $C_1$-$C_{30}$ aryl, or $C_1$-$C_{30}$ alkylaryl. The polysiloxane blocks corresponding to formula (28) are derived from the corresponding dihydroxy compound of formula (29):

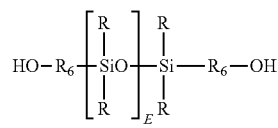
(29)

wherein R and E and $R_6$ are as described for formula (28).

In a specific embodiment, the polydiorganosiloxane blocks are derived from a polysiloxane monomer having the structure (30):

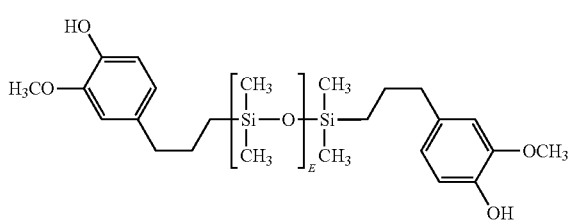
(30)

wherein E is an average value of between 20 and 75.

In another specific embodiment, the polydiorganosiloxane blocks are derived from a polysiloxane monomer having the structure (31):

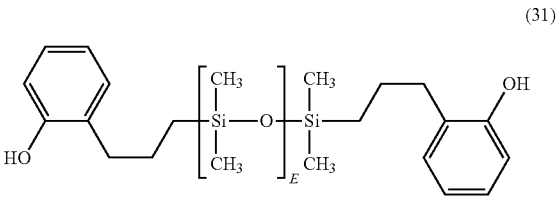
(31)

wherein E is an average value of between 20 and 75.

In a specific embodiment, the polydiorganosiloxane blocks are provided by repeating structural units of formula (32):

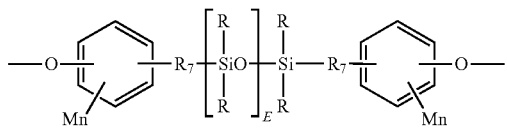
(32)

wherein R and E are as defined above. $R_7$ in formula (32) is a divalent $C_2$-$C_8$ aliphatic group. Each M in formula (32) can be the same or different, and is a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ aralkyl, $C_7$-$C_{12}$ aralkoxy, $C_7$-$C_{12}$ alkylaryl, or $C_7$-$C_{12}$ alkylaryloxy, wherein each n is independently 0, 1, 2, 3, or 4.

In one embodiment, M of formula (32) is bromo or chloro, an alkyl group such as methyl, ethyl, or propyl, an alkoxy group such as methoxy, ethoxy, or propoxy, or an aryl group such as phenyl, chlorophenyl, or tolyl; n is 0 to 4; $R_7$ is a dimethylene, trimethylene or tetramethylene group; and R is a $C_1$-$C_8$ alkyl, haloalkyl such as trifluoropropyl, cyanoalkyl, or aryl such as phenyl, chlorophenyl or tolyl. In another embodiment, R is methyl, or a combination of methyl and trifluoropropyl, or a combination of methyl and phenyl. In still another embodiment, M is methoxy, n is one, $R_7$ is a divalent $C_1$-$C_3$ aliphatic group, and R is methyl.

Polysiloxane-polycarbonates comprising units of formula (32) can be derived from the corresponding dihydroxy polydiorganosiloxane (33):

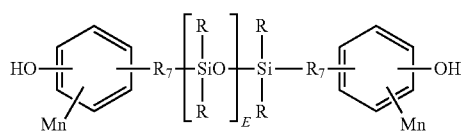

(33)

wherein each of R, E, M, $R_7$, and n are as described above. Such dihydroxy polysiloxanes can be made by affecting a platinum-catalyzed addition between a siloxane hydride of formula (34):

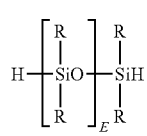

(34)

wherein R and E are as previously defined, and an aliphatically unsaturated monohydric phenol. Exemplary aliphatically unsaturated monohydric phenols included, for example, eugenol, 2-allylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl-4-propylphenol, 2-allyl-4,6-dimethylphenol, 2-allyl-4-bromo-6-methylphenol, 2-allyl-6-methoxy-4-methylphenol, 4-allylphenol, and 2-allyl-4,6-dimethylphenol. Combinations comprising at least one of the foregoing can also be used.

(vi) Methods of Making Polycarbonates

Polycarbonates may be manufactured by processes such as interfacial polymerization and melt polymerization. High Tg copolycarbonates are generally manufactured using interfacial polymerization. Although the reaction conditions for interfacial polymerization can vary, an exemplary process generally involves dissolving or dispersing one or more dihydric phenol reactants, such as a monomer of formula (I), in aqueous caustic soda or potash, adding the resulting mixture to a water-immiscible solvent medium, and contacting the reactants with a carbonate precursor in the presence of a catalyst such as, for example, a tertiary amine or a phase transfer catalyst, under controlled pH conditions, e.g., 8 to 11. The most commonly used water immiscible solvents include methylene chloride, 1,2-dichloroethane, chlorobenzene, toluene, and the like.

Exemplary carbonate precursors may include, for example, a carbonyl halide such as carbonyl dibromide or carbonyl dichloride (also known as phosgene), or a haloformate such as a bishaloformate of a dihydric phenol (e.g., the bischloroformate of bisphenol-A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In certain embodiments, the carbonate precursor is phosgene, a triphosgene, diacyl halide, dihaloformate, dicyanate, diester, diepoxy, diarylcarbonate, dianhydride, dicarboxylic acid, diacid chloride, or any combination thereof. An interfacial polymerization reaction to form carbonate linkages may use phosgene as a carbonate precursor, and is referred to as a phosgenation reaction.

Among tertiary amines that can be used are aliphatic tertiary amines such as triethylamine, tributylamine, cycloaliphatic amines such as N,N-diethyl-cyclohexylamine and aromatic tertiary amines such as N,N-dimethylaniline.

Among the phase transfer catalysts that can be used are catalysts of the formula $(R^{30})_4Q^+X$, wherein each $R^{30}$ is the same or different, and is a $C_1$-$C_{10}$ alkyl group; Q is a nitrogen or phosphorus atom; and X is a halogen atom, $C_1$-$C_8$ alkoxy group, or $C_6$-$C_{18}$ aryloxy group. Exemplary phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cl^-$, $Br^-$, a $C_1$-$C_8$ alkoxy group or a $C_6$-$C_{18}$ aryloxy group. An effective amount of a phase transfer catalyst can be 0.1 to 10 wt % based on the weight of bisphenol in the phosgenation mixture. For example, an effective amount of phase transfer catalyst can be 0.5 to 2 wt % based on the weight of bisphenol in the phosgenation mixture.

The polycarbonate may be prepared by a melt polymerization process. Generally, in the melt polymerization process, polycarbonates are prepared by co-reacting, in a molten state, the dihydroxy reactant(s) (e.g., aliphatic diol and/or aliphatic diacid, and any additional dihydroxy compound) and a diaryl carbonate ester, such as diphenyl carbonate, or more specifically in an embodiment, an activated carbonate such as bis (methyl salicyl)carbonate, in the presence of a transesterification catalyst. The reaction may be carried out in typical polymerization equipment, such as one or more continuously stirred reactors (CSTR's), plug flow reactors, wire wetting fall polymerizers, free fall polymerizers, wiped film polymerizers, BANBURY® mixers, single or twin screw extruders, or combinations of the foregoing. Volatile monohydric phenol is removed from the molten reactants by distillation and the polymer is isolated as a molten residue. A specifically useful melt process for making polycarbonates uses a diaryl carbonate ester having electron-withdrawing substituents on the aryls. Examples of specifically useful diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl)carbonate, bis(2-acetylphenyl) carboxylate, bis(4-acetylphenyl)carboxylate, or a combination comprising at least one of the foregoing.

The reactants for the polymerization reaction using an activated aromatic carbonate can be charged into a reactor either in the solid form or in the molten form. Initial charging of reactants into a reactor and subsequent mixing of these materials under reactive conditions for polymerization may be conducted in an inert gas atmosphere such as a nitrogen atmosphere. The charging of one or more reactants may also be done at a later stage of the polymerization reaction. Mixing of the reaction mixture is accomplished by any methods known in the art, such as by stirring. Reactive conditions include time, temperature, pressure and other factors that affect polymerization of the reactants. Typically the activated aromatic carbonate is added at a mole ratio of 0.8 to 1.3, and more preferably 0.9 to 1.3, and all sub-ranges there between, relative to the total moles of monomer unit compounds. In a specific embodiment, the molar ratio of activated aromatic carbonate to monomer unit compounds is 1.013 to 1.29, specifically 1.015 to 1.028.

(vii) End Capping Agents

All types of polycarbonate end groups are contemplated as being useful in the polycarbonates, including the high and low Tg polycarbonates, provided that such end groups do not significantly adversely affect desired properties of the compositions. An end-capping agent (also referred to as a chain-stopper) can be used to limit molecular weight growth rate, and so control molecular weight of the polycarbonate. Exemplary chain-stoppers include certain monophenolic compounds (i.e., phenyl compounds having a single free hydroxy group), monocarboxylic acid chlorides, and/or monochloroformates. Phenolic chain-stoppers are exemplified by phenol and $C_1$-$C_{22}$ alkyl-substituted phenols such as p-cumyl-phenol, resorcinol monobenzoate, and p-tertiary-butylphenol, cresol, and monoethers of diphenols, such as p-methoxyphenol. Exemplary chain-stoppers also include cyanophenols, such as for example, 4-cyanophenol, 3-cyanophenol, 2-cyanophenol, and polycyanophenols. Alkyl-substituted phenols with branched chain alkyl substituents having 8 to 9 carbon atoms can be specifically be used. Hydroxybenzophenones can be used.

Endgroups can be derived from the carbonyl source (i.e., the diaryl carbonate), from selection of monomer ratios, incomplete polymerization, chain scission, and the like, as well as any added end-capping groups, and can include derivatizable functional groups such as hydroxy groups, carboxylic acid groups, or the like. In an embodiment, the end-group of a polycarbonate can comprise a structural unit derived from a diaryl carbonate, where the structural unit can be an endgroup. In a further embodiment, the endgroup is derived from an activated carbonate. Such endgroups can derive from the transesterification reaction of the alkyl ester of an appropriately substituted activated carbonate, with a hydroxy group at the end of a polycarbonate polymer chain, under conditions in which the hydroxy group reacts with the ester carbonyl from the activated carbonate, instead of with the carbonate carbonyl of the activated carbonate. In this way, structural units derived from ester containing compounds or substructures derived from the activated carbonate and present in the melt polymerization reaction can form ester endgroups. In an embodiment, the ester endgroup derived from a salicylic ester can be a residue of bis(methyl salicyl) carbonate (BMSC) or other substituted or unsubstituted bis (alkyl salicyl)carbonate such as bis(ethyl salicyl)carbonate, bis(propyl salicyl)carbonate, bis(phenyl salicyl)carbonate, bis(benzyl salicyl)carbonate, or the like. In a specific embodiment, where BMSC is used as the activated carbonyl source, the endgroup is derived from and is a residue of BMSC, and is an ester endgroup derived from a salicylic acid ester, having the structure of formula (35):

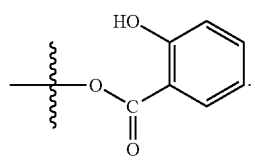

(35)

(viii) Branching Groups

Polycarbonates with branching groups are also contemplated as being useful, provided that such branching does not significantly adversely affect desired properties of the polycarbonate. Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl)alpha,alpha-dimethyl benzyl)phenol), 4-chloroformyl phthalic anhydride, trimesic acid, and benzophenone tetracarboxylic acid. The branching agents can be added at a level of about 0.05 to about 6.0 wt %. Mixtures comprising linear polycarbonates and branched polycarbonates can be used.

(B) Other Polymers

Other polymers that can be prepared from the monomers of formula (I), and optionally one or more different monomers, include, but are not limited to, polyesters; polyesteramides; polyetherimides; polyethers; polyethersulfones; polyepoxides; and combinations thereof. Polymerization of the monomers to these polymer types can be accomplished by any methods known in the art.

5. BLEND COMPOSITIONS

The polymers comprising repeating units derived from monomers of formula (I), as described above, can be used in blend compositions. The blend compositions may comprise one or more polymers comprising repeating units derived from monomers of formula (I). The blend compositions may comprise one or more additional polymers comprising repeating units derived from monomers other than the monomers of formula (I). The blend compositions may comprise additional components, such as one or more additives.

In certain embodiments, a blend composition comprises a first polymer (Polymer A) and a second polymer (Polymer B), and optionally one or more additives. The first polymer may be any polymer comprising repeating units derived from monomers of formula (I), such as a polymer as described above. The second polymer may be any polymer different from the first polymer that is suitable for use in a blend composition. In certain embodiments, the second polymer may be a polycarbonate, a polyester, a polysiloxane, a polyesteramide, a polyimide, a polyetherimide, a polyamideimide, a polyether, a polyethersulfone, a polyepoxide, a polylactide, a polylactic acid (PLA), or any combination thereof. In certain embodiments, the second polymer may be a vinyl polymer, a rubber-modified graft copolymer, an acrylic polymer, polyacrylonitrile, a polystyrene, a polyolefin, a polyester, a polyesteramide, a polysiloxane, a polyurethane, a polyamide, a polyamideimide, a polysulfone, a polyepoxide, a polyether, a polyimide, a polyetherimide, a polyphenylene ether, a polyphenylene sulfide, a polyether ketone, a polyether ether ketone, an ABS resin, an ASA resin, a polyethersulfone, a polyphenylsulfone, a poly(alkenylaromatic) polymer, a polybutadiene, a polyacetal, a polycarbonate, a polyphenylene ether, an ethylene-vinyl acetate copolymer, a polyvinyl acetate, a liquid crystal polymer, an ethylene-tetrafluoroethylene copolymer, an aromatic polyester, a polyvinyl fluoride, a polyvinylidene fluoride, a polyvinylidene chloride, tetrafluoroethylene, a polylactide, a polylactic acid (PLA), a polycarbonate-polyorganosiloxane block copolymer, or a copolymer comprising: (i) an aromatic ester, (ii) an estercarbonate, and (iii) carbonate repeat units. In certain embodiments, the second polymer is derived from one or more monomer units other than monomer units of formula (I). The blend composition may comprise additional polymers (e.g. a third, fourth, fifth, sixth, etc., polymer).

In a preferred embodiment, a blend composition comprises a combination of a first polycarbonate (Polymer A) comprising at least one repeating unit derived from a monomer of formula (I); and a second polycarbonate (Polymer B), wherein the second polycarbonate is different from the first polycarbonate. The first polycarbonate may be a high heat polycarbonate, as described above. The second polycarbonate may be a homopolycarbonate, a copolycarbonate, a polycarbonate-polysiloxane copolymer, a polyester-polycarbonate, or any combination thereof. In certain embodiments, the second polycarbonate comprises repeating units derived from monomers other than the monomers of formula (I). In certain embodiments, the second polycarbonate comprises repeating units derived from 2,2-bis(4-hydroxyphenyl)propane (bisphenol-A). Optionally, the blend composition further comprises at least one additive (C). In a preferred embodiment, the blend composition comprises a flame-retardant/anti-drip agent, a flame retardant additive, and/or an impact modifier. The flame-retardant/anti-drip agent may comprise a perfluorinated polyolefin.

In another preferred embodiment, a blend composition comprises a combination of a polycarbonate (Polymer A) comprising at least one repeating unit derived from a monomer of formula (I); and a polylactide (Polymer B). The polycarbonate may be a high heat polycarbonate, as described above. In certain embodiments, the polylactide comprises repeating units derived from monomers other than the monomers of formula (I). Optionally, the blend composition further comprises at least one additive (C). In a preferred embodiment, the blend composition comprises a flame-retardant/anti-drip agent, a flame retardant additive, and/or an impact modifier. The flame-retardant/anti-drip agent may comprise a perfluorinated polyolefin.

(A) First Polymer (Polymer A)

The first polymer (Polymer A) may be any polymer as described above, wherein the polymer comprises at least one repeating unit derived from a monomer of formula (I). The first polymer may be, in particular, a polycarbonate comprising repeating units derived from monomers of formula (I). The polycarbonate may be, for example, a homopolycarbonate, a copolycarbonate, an isosorbide-containing polycarbonate, a polyester-polycarbonate, or a polycarbonate polysiloxane, each optionally including end caps and/or branching groups, as described above.

(B) Second Polymer (Polymer B)

The second polymer (Polymer B) may be any polymer different from the first polymer that is suitable for use in a blend composition. For example, the second polymer may be a polycarbonate, a polyester, a polysiloxane, a polyesteramide, a polyimide, a polyetherimide, a polyamideimide, a polyether, a polyethersulfone, a polyepoxide, a polylactide, a polylactic acid (PLA), or any combination thereof.

In certain embodiments, the second polymer may be a vinyl polymer, a rubber-modified graft copolymer, an acrylic polymer, polyacrylonitrile, a polystyrene, a polyolefin, a polyester, a polyesteramide, a polysiloxane, a polyurethane, a polyamide, a polyamideimide, a polysulfone, a polyepoxide, a polyether, a polyimide, a polyetherimide, a polyphenylene ether, a polyphenylene sulfide, a polyether ketone, a polyether ether ketone, an ABS resin, an ASA resin, a polyethersulfone, a polyphenylsulfone, a poly(alkenylaromatic) polymer, a polybutadiene, a polyacetal, a polycarbonate, a polyphenylene ether, an ethylene-vinyl acetate copolymer, a polyvinyl acetate, a liquid crystal polymer, an ethylene-tetrafluoroethylene copolymer, an aromatic polyester, a polyvinyl fluoride, a polyvinylidene fluoride, a polyvinylidene chloride, tetrafluoroethylene, a polylactide, a polylactic acid (PLA), a polycarbonate-polyorganosiloxane block copolymer, or a copolymer comprising: (i) an aromatic ester, (ii) an estercarbonate, and (iii) carbonate repeat units.

In certain embodiments, the second polymer is derived from one or more monomer units other than monomer units of formula (I).

In certain embodiments, the second polymer may be a polycarbonate derived from monomer units of formula (I), other monomers, and any combination thereof. In certain embodiments, the second polymer may be a polycarbonate derived from monomer units other than monomer units of formula (I).

In a preferred embodiment, the second polymer may be a polycarbonate derived from one or more of the monomer units disclosed herein, except for the monomer units of formula (I). For example, the second polymer may comprise repeating units of formula (2), as described above, which may be derived from dihydroxy monomer units of formula (4).

(C) Additives

The blend compositions may comprise additional components, such as one or more additives. Suitable additives include, but are not limited to impact modifiers, UV stabilizers, colorants, flame retardants, heat stabilizers, plasticizers, lubricants, mold release agents, fillers, reinforcing agents, antioxidant agents, antistatic agents, blowing agents, anti-drip agents, and radiation stabilizers.

(i) Impact Modifiers

The blend composition may comprise impact modifiers. For example, the composition can further include impact modifier(s), with the proviso that the additives are selected so as to not significantly adversely affect the desired properties of the composition. Suitable impact modifiers may be high molecular weight elastomeric materials derived from olefins, monovinyl aromatic monomers, acrylic and methacrylic acids and their ester derivatives, as well as conjugated dienes. The blend composition formed from conjugated dienes can be fully or partially hydrogenated. The elastomeric materials can be in the form of homopolymers or copolymers, including random, block, radial block, graft, and core-shell copolymers. Combinations of impact modifiers may be used.

A specific type of impact modifier may be an elastomer-modified graft copolymer comprising (i) an elastomeric (i.e., rubbery) polymer substrate having a Tg less than about 10° C., less than about 0° C., less than about −10° C., or between about −40° C. to −80° C., and (ii) a rigid polymer grafted to the elastomeric polymer substrate. Materials suitable for use as the elastomeric phase include, for example, conjugated diene rubbers, for example polybutadiene and polyisoprene; copolymers of a conjugated diene with less than about 50 wt % of a copolymerizable monomer, for example a monovinylic compound such as styrene, acrylonitrile, n-butyl acrylate, or ethyl acrylate; olefin rubbers such as ethylene propylene copolymers (EPR) or ethylene-propylene-diene monomer rubbers (EPDM); ethylene-vinyl acetate rubbers; silicone rubbers; elastomeric $C_1$-$C_8$ alkyl(meth)acrylates; elastomeric copolymers of $C_1$-$C_8$ alkyl(meth)acrylates with butadiene and/or styrene; or combinations comprising at least one of the foregoing elastomers. Materials suitable for use as the rigid phase include, for example, monovinyl aromatic monomers such as styrene and alpha-methyl styrene, and monovinylic monomers such as acrylonitrile, acrylic acid, methacrylic acid, and the $C_1$-$C_6$ esters of acrylic acid and methacrylic acid, specifically methyl methacrylate.

Specific impact modifiers include styrene-butadiene-styrene (SBS), styrene-butadiene rubber (SBR), styrene-ethylene-butadiene-styrene (SEBS), ABS (acrylonitrile-butadiene-styrene), acrylonitrile-ethylene-propylene-diene-styrene (AES), styrene-isoprene-styrene (SIS), methyl methacrylate-butadiene-styrene (MBS), and styrene-acrylonitrile (SAN). Exemplary elastomer-modified graft copolymers include those formed from styrene-butadiene-styrene (SBS), styrene-butadiene rubber (SBR), styrene-ethylene-butadiene-styrene (SEBS), ABS (acrylonitrile-butadiene-styrene), acrylonitrile-ethylene-propylene-diene-styrene (AES), styrene-isoprene-styrene (SIS), methyl methacrylate-butadiene-styrene (MBS), and styrene-acrylonitrile (SAN).

MBS may be derived from the following monomers:

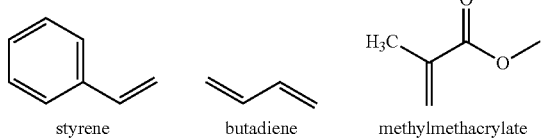

SEBS may be a linear triblockcopolymer based on styrene and ethylene/butylene. Each copolymer chain may consist of three blocks: a middle block that is a random ethylene/butylene copolymer surrounded by two blocks of polystyrene. The SEBS may be styrene-b-(ethylene-co-butylene)-b-styrene polymer.

Impact modifiers may be present in amounts of 1 to 30 parts by weight, based on 100 parts by weight of the polymer component of the blend composition. Preferred impact modifiers may include MBS and SBS.

(ii) UV Stabilizers

The blend composition may comprise a UV stabilizer for improved performance in UV stabilization. UV stabilizers disperse UV radiation energy.

UV stabilizers may be hydroxybenzophenones, hydroxyphenyl benzotriazoles, cyanoacrylates, oxanilides, and hydroxyphenyl triazines. UV stabilizers may include, but are not limited to, poly[(6-morphilino-s-triazine-2,4-diyl)[2,2,6,6-tetramethyl-4-piperidyl)imino]-hexamethylene[(2,2,6,6-tetramethyl-4-piperidyl)imino], 2-hydroxy-4-octyloxybenzophenone (Uvinul®3008), 6-tert-butyl-2-(5-chloro-2H-benzotriazole-2-yl)-4-methylphenyl (Uvinul® 3026), 2,4-di-tert-butyl-6-(5-chloro-2H-benzotriazole-2-yl)-phenol (Uvinul®3027), 2-(2H-benzotriazole-2-yl)-4,6-di-tert-pentylphenol (Uvinul®3028), 2-(2H-benzotriazole-2-yl)-4-(1,1,3,3-tetramethylbutyl)-phenol (Uvinul® 3029), 1,3-bis[(2'-cyano-3',3'-diphenylacryloyl)oxy]-2,2-bis-{[(2'-cyano-3',3'-diphenylacryloyl)oxy]methyl}-propane (Uvinul® 3030), 2-(2H-benzotriazole-2-yl)-4-methylphenol (Uvinul® 3033), 2-(2H-benzotriazole-2-yl)-4,6-bis(1-methyl-1-phenyethyl) phenol (Uvinul® 3034), ethyl-2-cyano-3,3-diphenylacrylate (Uvinul® 3035), (2-ethylhexyl)-2-cyano-3,3-diphenylacrylate (Uvinul® 3039), N,N'-bisformyl-N,N'-bis(2,2,6,6-tetramethyl-4-piperidinyl)hexamethylendiamine (Uvinul® 4050H), bis-(2,2,6,6-tetramethyl-4-pipieridyl)-sebacate (Uvinul® 4077H), bis-(1,2,2,6,6-pentamethyl-4-piperdiyl)-sebacate+methyl-(1,2,2,6,6-pentamethyl-4-piperidyl)-sebacate (Uvinul® 4092H) or combination thereof.

The blend composition may comprise one or more UV stabilizers, including Cyasorb 5411, Cyasorb UV-3638, Uvinul 3030, and/or Tinuvin 234.

Certain monophenolic UV absorbers, which can also be used as capping agents, can be utilized as one or more additives; for example, 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives, and the like.

(iii) Colorants

The blend composition may comprise colorants such as pigment and/or dye additives. Useful pigments may include, for example, inorganic pigments such as metal oxides and mixed metal oxides such as zinc oxide, titanium dioxides, iron oxides, or the like; sulfides such as zinc sulfides, or the like; aluminates; sodium sulfo-silicates sulfates, chromates, or the like; carbon blacks; zinc ferrites; ultramarine blue; organic pigments such as azos, di-azos, quinacridones, perylenes, naphthalene tetracarboxylic acids, flavanthrones, isoindolinones, tetrachloroisoindolinones, anthraquinones, enthrones, dioxazines, phthalocyanines, and azo lakes; Pigment Red 101, Pigment Red 122, Pigment Red 149, Pigment Red 177, Pigment Red 179, Pigment Red 202, Pigment Violet 29, Pigment Blue 15, Pigment Blue 60, Pigment Green 7, Pigment Yellow 119, Pigment Yellow 147, Pigment Yellow 150, and Pigment Brown 24; or combinations comprising at least one of the foregoing pigments. Pigments are generally used in amounts of 0.01 to 10 parts by weight, based on 100 parts by weight of the polymer component of the blend composition.

Exemplary dyes are generally organic materials and include, for example, coumarin dyes such as coumarin 460 (blue), coumarin 6 (green), nile red or the like; lanthanide complexes; hydrocarbon and substituted hydrocarbon dyes; polycyclic aromatic hydrocarbon dyes; scintillation dyes such as oxazole or oxadiazole dyes; aryl- or heteroaryl-substituted poly($C_2$-$C_8$) olefin dyes; carbocyanine dyes; indanthrone dyes; phthalocyanine dyes; oxazine dyes; carbostyryl dyes; napthalenetetracarboxylic acid dyes; porphyrin dyes; bis(styryl)biphenyl dyes; acridine dyes; anthraquinone dyes; cyanine dyes; methine dyes; arylmethane dyes; azo dyes; indigoid dyes, thioindigoid dyes, diazonium dyes; nitro dyes; quinone imine dyes; aminoketone dyes; tetrazolium dyes; thiazole dyes; perylene dyes, perinone dyes; bis-benzoxazolylthiophene (BBOT); triarylmethane dyes; xanthene dyes; thioxanthene dyes; naphthalimide dyes; lactone dyes; fluorophores such as anti-stokes shift dyes which absorb in the near infrared wavelength and emit in the visible wavelength, or the like; luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3"",5""-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H-pyran; 1,1'-diethyl-2,2'-carbocyanine iodide; 3,3'-diethyl-4,4',5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene, chrysene, rubrene, coronene, or the like; or combinations comprising at least one of the foregoing dyes. Dyes are generally used in amounts of 0.01 to 10 parts by weight, based on 100 parts by weight of the polymer component of the blend composition.

(iv) Flame Retardants

The blend composition may comprise flame retardants. Various types of flame retardants can also be utilized as additives. In one embodiment, the flame retardant additives include, for example, flame retardant salts such as alkali metal salts of perfluorinated $C_1$-$C_{16}$ alkyl sulfonates such as potassium perfluorobutane sulfonate (Rimar salt), potassium perfluoroctane sulfonate, tetraethylammonium perfluorohexane sulfonate, potassium diphenylsulfone sulfonate (KSS), and the like, sodium benzene sulfonate, sodium toluene sulfonate (NATS) and the like; and salts formed by reacting for example an alkali metal or alkaline earth metal (for example lithium, sodium, potassium, magnesium, calcium and barium salts) and an inorganic acid complex salt, for example, an oxo-anion, such as alkali metal and alkaline-earth metal salts of carbonic acid, such as $Na_2CO_3$, $K_2CO_3$, $MgCO_3$, $CaCO_3$, and $BaCO_3$ or fluoro-anion complex such as $Li_3AlF_6$, $BaSiF_6$, $KBF_4$, $K_3AlF_6$, $KAlF_4$, $K_2SiF_6$, and/or $Na_3AlF_6$ or the like. Rimar salt and KSS and NATS, alone or in combination with other flame retardants, are particularly useful in the blend compositions disclosed herein.

The flame retardants may be selected from at least one of the following: alkali metal salts of perfluorinated $C_1$-$C_{16}$ alkyl sulfonates; potassium perfluorobutane sulfonate; potassium perfluoroctane sulfonate; tetraethylammonium perfluorohexane sulfonate; and potassium diphenylsulfone sulfonate.

The flame retardant additives may include organic compounds that include phosphorus, bromine, and/or chlorine.

In certain embodiments, the flame retardant is not a bromine or chlorine containing composition. Non-brominated and non-chlorinated phosphorus-containing flame retardants can be used in certain applications for regulatory reasons, for example organic phosphates and organic compounds containing phosphorus-nitrogen bonds. One type of exemplary organic phosphate is an aromatic phosphate of the formula $(GO)_3P=O$, wherein each G is independently an alkyl, cycloalkyl, aryl, alkylaryl, or arylalkyl group, provided that at least one G is an aromatic group. Two of the G groups can be joined together to provide a cyclic group, for example, diphenyl pentaerythritol diphosphate. Exemplary aromatic phosphates include, phenyl bis(dodecyl)phosphate, phenyl bis(neopentyl)phosphate, phenyl bis(3,5,5'-trimethylhexyl) phosphate, ethyl diphenyl phosphate, 2-ethylhexyl di(p-tolyl) phosphate, bis(2-ethylhexyl) p-tolyl phosphate, tritolyl phosphate, bis(2-ethylhexyl)phenyl phosphate, tri(nonylphenyl)phosphate, bis(dodecyl) p-tolyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or poly-functional aromatic phosphorus-containing compounds are also useful as additives, for example, compounds of the formulas (36), (37), and (38):

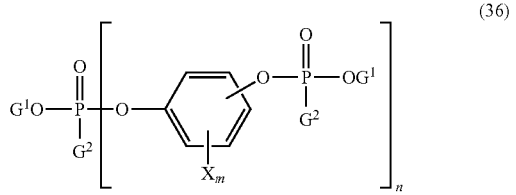

(36)

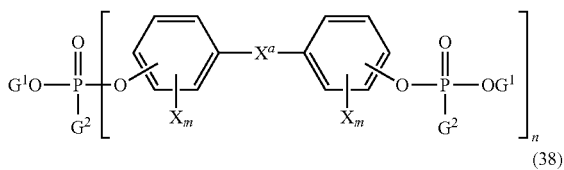

(37)

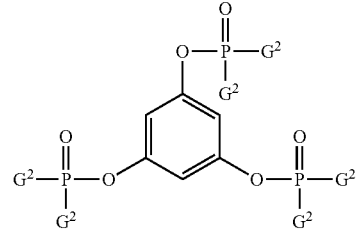

(38)

wherein each $G^1$ is independently a hydrocarbon having 1 to 30 carbon atoms; each $G^2$ is independently a hydrocarbon or hydrocarbonoxy having 1 to 30 carbon atoms; each X is independently a bromine or chlorine; m is 0 to 4, and n is 1 to 30. Exemplary di- or polyfunctional aromatic phosphorus-containing compounds include resorcinol tetraphenyl diphosphate (RDP), the bis(diphenyl)phosphate of hydroquinone and the bis(diphenyl) phosphate of bisphenol-A, respectively, their oligomeric and polymeric counterparts, and the like.

Exemplary flame retardant additives containing phosphorus-nitrogen bonds include phosphonitrilic chloride, phosphorus ester amides, phosphoric acid amides, phosphonic acid amides, phosphinic acid amides, and tris(aziridinyl) phosphine oxide.

The flame retardant additive may have formula (39):

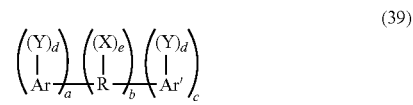

(39)

wherein R is a $C_1$-$C_{36}$ alkylene, alkylidene or cycloaliphatic linkage, e.g., methylene, ethylene, propylene, isopropylene, isopropylidene, butylene, isobutylene, amylene, cyclohexylene, cyclopentylidene, or the like; or an oxygen ether, carbonyl, amine, or a sulfur-containing linkage, e.g., sulfide, sulfoxide, sulfone, or the like. R can also consist of two or more alkylene or alkylidene linkages connected by such groups as aromatic, amino, ether, carbonyl, sulfide, sulfoxide, sulfone, or the like.

Ar and Ar' in formula (39) are each independently mono- or polycarbocyclic aromatic groups such as phenylene, biphenylene, terphenylene, naphthylene, or the like.

Y is an organic, inorganic, or organometallic radical, for example halogen, e.g., chlorine, bromine, iodine, fluorine; ether groups of the general formula OB, wherein B is a monovalent hydrocarbon group similar to X; monovalent hydrocarbon groups of the type represented by R; or other substituents, e.g., nitro, cyano, and the like, said substituents being essentially inert provided that there is greater than or equal to one, specifically greater than or equal to two, halogen atoms per aryl nucleus. One or both of Ar and Ar' may further have one or more hydroxyl substituents.

When present, each X is independently a monovalent hydrocarbon group, for example an alkyl group such as methyl, ethyl, propyl, isopropyl, butyl, decyl, or the like; an aryl group such as phenyl, naphthyl, biphenyl, xylyl, tolyl, or the like; an aralkyl group such as benzyl, ethylphenyl, or the like; or a cycloaliphatic group such as cyclopentyl, cyclohexyl, or the like. The monovalent hydrocarbon group can itself contain inert substituents.

Each d is independently 1 to a maximum equivalent to the number of replaceable hydrogens substituted on the aromatic rings comprising Ar or Ar'. Each e is independently 0 to a maximum equivalent to the number of replaceable hydrogens on R. Each a, b, and c is independently a whole number, including 0. When b is not 0, neither a nor c can be 0. Otherwise either a or c, but not both, can be 0. Where b is 0, the aromatic groups are joined by a direct carbon-carbon bond.

The hydroxyl and Y substituents on the aromatic groups, Ar and Ar' can be varied in the ortho, meta or para positions on the aromatic rings and the groups can be in any possible geometric relationship with respect to one another.

Included within the scope of polymeric or oligomeric flame retardants derived from mono or dihydroxy derivatives of formula (39) are: 2,2-bis-(3,5-dichlorophenyl)-propane; bis-(2-chlorophenyl)-methane; bis(2,6-dibromophenyl)-methane; 1,1-bis-(4-iodophenyl)-ethane; 1,2-bis-(2,6-dichlorophenyl)-ethane; 1,1-bis-(2-chloro-4-iodophenyl)ethane; 1,1-bis-(2-chloro-4-methylphenyl)-ethane; 1,1-bis-(3,5-dichlorophenyl)-ethane; 2,2-bis-(3-phenyl-4-bromophenyl)-ethane; 2,6-bis-(4,6-dichloronaphthyl)-propane; 2,2-bis-(2,6-dichlorophenyl)-pentane; 2,2-bis-(3,5-dibromophenyl)-hexane; bis-(4-chlorophenyl)-phenyl-methane; bis-(3,5-dichlorophenyl)-cyclohexylmethane; bis-(3-nitro-4-bromophenyl)-methane; bis-(4-hydroxy-2,6-dichloro-3-methoxyphenyl)-methane; 2,2-bis-(3,5-dichloro-4-hydroxyphenyl)-propane; and 2,2-bis-(3-bromo-4-hydroxyphenyl)-propane. Also included within the above structural formula are: 1,3-dichlorobenzene, 1,4-dibromobenzene, 1,3-dichloro-4-hydroxybenzene, and biphenyls such as 2,2'-dichlorobiphenyl, polybrominated 1,4-diphenoxybenzene, 2,4'-dibromobiphenyl, and 2,4'-dichlorobiphenyl as well as decabromo diphenyl oxide, and the like.

Another useful class of flame retardant is the class of cyclic siloxanes having the general formula $[(R)_2SiO]_y$ wherein R is a monovalent hydrocarbon or fluorinated hydrocarbon having from 1 to 18 carbon atoms and y is a number from 3 to 12. Examples of fluorinated hydrocarbon include, but are not limited to, 3-fluoropropyl, 3,3,3-trifluoropropyl, 5,5,5,4,4,3,3-heptafluoropentyl, fluorophenyl, difluorophenyl and trifluorotolyl. Examples of suitable cyclic siloxanes include, but are not limited to, octamethylcyclotetrasiloxane, 1,2,3,4-tetramethyl-1,2,3,4-tetravinylcyclotetrasiloxane, 1,2,3,4-tetramethyl-1,2,3,4-tetraphenylcyclotetrasiloxane, octaethylcyclotetrasiloxane, octapropylcyclotetrasiloxane, octabutylcyclotetrasiloxane, decamethylcyclopentasiloxane, dodecamethylcyclohexasiloxane, tetradecamethylcycloheptasiloxane, hexadecamethylcyclooctasiloxane, eicosamethylcyclodecasiloxane, octaphenylcyclotetrasiloxane, and the like. A particularly useful cyclic siloxane is octaphenylcyclotetrasiloxane.

When present, the foregoing flame retardant additives are generally present in amounts of 0.01 to 10 wt %, more specifically 0.02 to 5 wt %, based on 100 parts by weight of the polymer component of the blend composition.

(v) Heat Stabilizers

The blend composition may comprise heat stabilizers. Exemplary heat stabilizer additives include, for example, organophosphites such as triphenyl phosphite, tris-(2,6-dimethylphenyl)phosphite, tris-(mixed mono- and di-nonylphenyl)phosphite or the like; phosphonates such as dimethylbenzene phosphonate or the like; phosphates such as trimethyl phosphate, or the like; or combinations comprising at least one of the foregoing heat stabilizers. Heat stabilizers are generally used in amounts of 0.0001 to 1 part by weight, based on 100 parts by weight of the polymer component of the blend composition.

(vi) Plasticizers, Lubricants, Mold Release Agents

The blend composition may comprise plasticizers, lubricants, and mold release agents. Mold release agent (MRA) will allow the material to be removed quickly and effectively. Mold releases can reduce cycle times, defects, and browning of finished product. There is considerable overlap among these types of materials, which may include, for example, phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl)phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, e.g., methyl stearate, stearyl stearate, pentaerythritol tetrastearate (PETS), and the like; combinations of methyl stearate and hydrophilic and hydrophobic nonionic surfactants comprising polyethylene glycol polymers, polypropylene glycol polymers, poly(ethylene glycol-co-propylene glycol) copolymers, or a combination comprising at least one of the foregoing glycol polymers, e.g., methyl stearate and polyethylene-polypropylene glycol copolymer in a suitable solvent; waxes such as beeswax, montan wax, paraffin wax, or the like. Such materials are generally used in amounts of 0.001 to 1 part by weight, specifically 0.01 to 0.75 part by weight, more specifically 0.1 to 0.5 part by weight, based on 100 parts by weight of the polymer component of the blend composition.

(vii) Other Filler or ReInforcing Agents

The blend composition may comprise other fillers or reinforcing agents. Possible fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate (as its anhydride, dihydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix, or the like; single crystal fibers or "whiskers" such as silicon carbide, alumina, boron carbide, iron, nickel, copper, or the like; fibers (including continuous and chopped fibers) such as asbestos, carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like;

natural fillers and reinforcements, such as wood flour obtained by pulverizing wood, fibrous products such as cellulose, cotton, sisal, jute, starch, cork flour, lignin, ground nut shells, corn, rice grain husks or the like; organic fillers such as polytetrafluoroethylene; reinforcing organic fibrous fillers formed from organic polymers capable of forming fibers such as poly(ether ketone), polyimide, polybenzoxazole, poly (phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents.

The fillers and reinforcing agents can be coated with a layer of metallic material to facilitate conductivity, or surface treated with silanes to improve adhesion and dispersion with the polymeric matrix. In addition, the reinforcing fillers can be provided in the form of monofilament or multifilament fibers and can be used individually or in combination with other types of fiber, through, for example, co-weaving or core/sheath, side-by-side, orange-type or matrix and fibril constructions, or by other methods known to one skilled in the art of fiber manufacture. Exemplary co-woven structures include, for example, glass fiber-carbon fiber, carbon fiber-aromatic polyimide (aramid) fiber, and aromatic polyimide fiberglass fiber or the like. Fibrous fillers can be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids. Fillers are generally used in amounts of 0 to 80 parts by weight, based on 100 parts by weight of the polymer component of the blend composition.

(viii) Antioxidant Additives

The blend composition may comprise an antioxidant additive. Exemplary antioxidant additives include, for example, organophosphites such as tris(nonyl phenyl)phosphite, tris(2,4-di-t-butylphenyl)phosphite ("IRGAFOS 168" or "I-168"), bis(2,4-di-t-butylphenyl)pentaerythritol diphosphite, distearyl pentaerythritol diphosphite or the like; alkylated monophenols or polyphenols; alkylated reaction products of polyphenols with dienes, such as tetrakis[methylene(3,5-di-tert-butyl-4-hydroxyhydrocinnamate)]methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl) propionate or the like; amides of beta-(3,5-di-tert-butyl-4-hydroxyphenyl)-propionic acid or the like, or combinations comprising at least one of the foregoing antioxidants. Antioxidants are generally used in amounts of 0.0001 to 1 part by weight, based on 100 parts by weight of the polymer component of the blend composition.

(ix) Antistatic Agents

The blend composition may comprise an antistatic agent. Examples of monomeric antistatic agents may include glycerol monostearate, glycerol distearate, glycerol tristearate, ethoxylated amines, primary, secondary and tertiary amines, ethoxylated alcohols, alkyl sulfates, alkylarylsulfates, alkylphosphates, alkylaminesulfates, alkyl sulfonate salts such as sodium stearyl sulfonate, sodium dodecylbenzenesulfonate or the like, quaternary ammonium salts, quaternary ammonium resins, imidazoline derivatives, sorbitan esters, ethanolamides, betaines, or the like, or combinations comprising at least one of the foregoing monomeric antistatic agents.

Exemplary polymeric antistatic agents may include certain polyesteramides polyether-polyamide (polyetheramide) block copolymers, polyetheresteramide block copolymers, polyetheresters, or polyurethanes, each containing polyalkylene glycol moieties polyalkylene oxide units such as polyethylene glycol, polypropylene glycol, polytetramethylene glycol, and the like. Such polymeric antistatic agents are commercially available, for example PELESTAT® 6321 (Sanyo) or PEBAX® MH1657 (Atofina), IRGASTAT® P18 and P22 (Ciba-Geigy). Other polymeric materials may be used as antistatic agents are inherently conducting polymers such as polyaniline (commercially available as PANIPOL®EB from Panipol), polypyrrole and polythiophene (commercially available from Bayer), which retain some of their intrinsic conductivity after melt processing at elevated temperatures. Carbon fibers, carbon nanofibers, carbon nanotubes, carbon black, or a combination comprising at least one of the foregoing may be used in a polymeric resin containing chemical antistatic agents to render the composition electrostatically dissipative. Antistatic agents are generally used in amounts of 0.0001 to 5 parts by weight, based on 100 parts by weight of the polymer component of the blend composition.

(x) Blowing Agents

The blend composition may comprise a blowing agent. Foam may be a useful blowing agent. Low boiling halohydrocarbons and those that generate carbon dioxide may be used as blowing agents. Blowing agents may be used that are solid at room temperature and when heated to temperatures higher than their decomposition temperature, generate gases such as nitrogen, carbon dioxide, and ammonia gas, such as azodicarbonamide, metal salts of azodicarbonamide, 4,4' oxybis(benzenesulfonylhydrazide), sodium bicarbonate, ammonium carbonate, or the like, or combinations comprising at least one of the foregoing blowing agents. Blowing agents may be used in amounts of 0.01 to 20 parts by weight, based on 100 parts by weight of the polymer component of the blend composition.

(xi) Anti-Drip Agents

The blend composition may comprise anti-drip agents. The anti-drip agent may be a fibril forming or non-fibril forming fluoropolymer such as polytetrafluoroethylene (PTFE). The anti-drip agent can be encapsulated by a rigid copolymer as described above, for example styrene-acrylonitrile copolymer (SAN). PTFE encapsulated in SAN is known as TSAN. Encapsulated fluoropolymers can be made by polymerizing the encapsulating polymer in the presence of the fluoropolymer, for example an aqueous dispersion. TSAN can provide significant advantages over PTFE, in that TSAN can be more readily dispersed in the composition. An exemplary TSAN can comprise 50 wt % PTFE and 50 wt % SAN, based on the total weight of the encapsulated fluoropolymer. The SAN can comprise, for example, 75 wt % styrene and 25 wt % acrylonitrile based on the total weight of the copolymer. Alternatively, the fluoropolymer can be pre-blended in some manner with a second polymer, such as for, example, an aromatic polycarbonate or SAN to form an agglomerated material for use as an anti-drip agent. Either method can be used to produce an encapsulated fluoropolymer. Antidrip agents are generally used in amounts of 0.1 to 5 percent by weight, based on 100 parts by weight of the polymer component of the blend composition.

(xii) Radiation Stabilizers

The blend composition may comprise radiation stabilizers. The radiation stabilizer may be a gamma-radiation stabilizer. Exemplary gamma-radiation stabilizers include alkylene polyols such as ethylene glycol, propylene glycol, 1,3-propanediol, 1,2-butanediol, 1,4-butanediol, meso-2,3-butanediol, 1,2-pentanediol, 2,3-pentanediol, 1,4-pentanediol, 1,4-hexandiol, and the like; cycloalkylene polyols such as 1,2-cyclopentanediol, 1,2-cyclohexanediol, and the like; branched alkylenepolyols such as 2,3-dimethyl-2,3-butanediol (pinacol), and the like, as well as alkoxy-substituted cyclic or acyclic alkanes. Unsaturated alkenols are also useful, examples of which include 4-methyl-4-penten-2-ol, 3-methyl-pentene-3-ol, 2-methyl-4-penten-2-ol, 2,4-dimethyl-4-penten-2-ol, and 9 to decen-1-ol, as well as tertiary alcohols that have at least one hydroxy substituted tertiary carbon, for example 2-methyl-2,4-pentanediol (hexylene glycol), 2-phenyl-2-butanol, 3-hydroxy-3-methyl-2-butanone, 2-phenyl-2-butanol, and the like, and cyclic tertiary alcohols such as 1-hydroxy-1-methyl-cyclohexane. Certain hydroxymethyl aromatic compounds that have hydroxy substitution on a saturated carbon attached to an unsaturated carbon in an aromatic ring can also be used. The hydroxy-substituted saturated carbon can be a methylol group ($-CH_2OH$) or it can be a member of a more complex hydrocarbon group such as $-CR^{24}HOH$ or $-CR^{24}{}_2OH$ wherein $R^{24}$ is a complex or a simple hydrocarbon. Specific hydroxy methyl aromatic compounds include benzhydrol, 1,3-benzenedimethanol, benzyl alcohol, 4-benzyloxy benzyl alcohol and benzyl benzyl alcohol. 2-Methyl-2,4-pentanediol, polyethylene glycol, and polypropylene glycol are often used for gamma-radiation stabilization. Gamma-radiation stabilizing compounds are typically used in amounts of 0.1 to 10 parts by weight based on 100 parts by weight of the polymer component of the blend composition.

6. METHOD OF MAKING THE BLEND COMPOSITIONS

The blend composition can be manufactured by various methods. For example, the blend composition may be first blended in a high speed HENSCHEL-Mixer®. Other low shear processes, including but not limited to hand mixing, can also accomplish this blending. The blend may then be fed into the throat of a single or twin-screw extruder via a hopper. Alternatively, at least one of the components can be incorporated into the composition by feeding directly into the extruder at the throat and/or downstream through a side-stuffer. Additives can also be compounded into a masterbatch with a desired polymeric resin and fed into the extruder. The extruder may be generally operated at a temperature higher than that necessary to cause the composition to flow. The extrudate may be immediately quenched in a water batch and pelletized. The pellets, so prepared, when cutting the extrudate can be one-fourth inch long or less as desired. Such pellets can be used for subsequent molding, shaping, or forming.

7. ARTICLES

A polymer or blend composition, such as described above, may be formed, shaped, molded or injection molded into an article. The compositions can be molded into useful shaped articles by a variety of means such as injection molding, extrusion, rotational molding, blow molding and thermoforming to form articles such as, for example, various components for cell phones and cell phone covers, components for computer housings, computer housings and business machine housings such as housings for monitors, handheld electronic device housings such as computer or business machine housings, housings for hand-held devices, components for light fixtures or home appliances, components for medical applications or devices, components for interior or exterior components of an automobile, lenses (auto and non-auto) such as components for film applications, greenhouse components, sun room components, or fire helmets, and the like.

In certain embodiments, an article comprising a polymer or blend composition, as described above, may be selected from automotive bumpers, other automotive exterior components, automobile minor housings, automobile wheel covers, automobile instrument panels and trim, automobile glove boxes, automobile door hardware and other interior trim, automobile exterior lights, automobile parts within the engine compartment, plumbing equipment, valves and pumps, air conditioning heating and cooling parts, furnace and heat pump parts, computer parts, electronics parts, projector parts, electronic display parts, copier parts, scanner parts, electronic printer toner cartridges, hair driers, irons, coffee makers, toasters, washing machines, microwaves, ovens, power tools, electric components, lighting parts, dental instruments, medical instruments, cookware, medical instrument trays, animal cages, fibers, laser welded medical devices, and fiber optics.

In certain embodiments, the article may have a biocontent according to ASTM-D6866 of at least 2 weight %, at least 3 weight %, at least 4 weight %, at least 5 weight %, at least 6 weight %, at least 7 weight %, at least 8 weight %, at least 9 weight %, at least 10 weight %, at least 11 weight %, at least 12 weight %, at least 13 weight %, at least 14 weight %, at least 15 weight %, at least 16 weight %, at least 17 weight %, at least 18 weight %, at least 19 weight %, at least 20 weight %, at least 25 weight %, at least 30 weight %, at least 35 weight %, at least 40 weight %, at least 45 weight %, at least 50 weight %, at least 55 weight %, at least 60 weight %, or at least 65 weight %.

8. METHOD OF MAKING THE ARTICLES

The article may be produced by a manufacturing process. The process may comprise the steps of (a) providing a composition comprising one or more polymers as described above, wherein at least one of the polymers has at least some structural units derived from a monomer unit of formula (I). The composition from step (a) may then be (b) melted, for example, at 200-400° C., 225-350° C., 250-310° C., or 270-290° C. in an extruder. The melted composition of step (b) may then be (c) extruded, and (d) the composition may be isolated or chopped. The article of manufacture may further be produced by the step of (e) drying the composition. The article may have a melt volume rate (MVR) of 2 to 70 cubic centers (cc) per 10 minutes, more specifically 4 to 60 cc/10 min, using the ASTM D1238 method, 2.16 kg load, 330° C. temperature, 360 sec dwell.

The present invention has multiple aspects, illustrated by the following non-limiting examples.

9. EXAMPLES

Materials: All solvents and reagents used were analytical grade. 1-Indanone (99.98%) was purchased from Medical Chem. (Yancheng) Manf. Co. Ltd. Crotonic acid (98%), 3,3- dimethyl acrylic acid (97%), benzene (anhyd., 99.8%), and aluminium chloride (anhyd., 99%) were purchased from Aldrich. Phenol, toluene, and methanol (for HPLC, 99.8%) were purchased from Merck. Ethylacetate (99%), aqueous HCl (35%), and $H_2SO_4$ (98%) were purchased from Chemlab.

Instrumentation (HPLC, MS, NMR, DSC, GPC): Analysis of the monomer prep reaction materials were conducted by HPLC chromatography using C-18 reverse phase column chromatography with acetonitrile-methanol-water (0.02% $H_3PO_4$) as the mobile phase. Proton NMR was recorded on a Bruker 300 MHz spectrometer (sample was prepared in DMSO-$d_6$). LC/MS was recorded on a Waters photodiode array detector. Differential scanning calorimetry (DSC) was used to determine the melting point of the monomer. Molecular weight characterization of the polycarbonates used standard gel permeation chromatography techniques using divinylbenzene-crosslinked polystyrene columns and methylene chloride (spiked with toluene as a flow marker) as the elution solvent. Calibration was completed using polystyrene standards referenced to polycarbonate. Differential scanning calorimetry employing a temperature sweep rate of 20° C./min was used to determine glass transition temperatures of the polycarbonates.

Example 1

4,4'-(3,3-dimethyl-2,2-dihydro-1H-indene-1,1-diyl)diphenol ("DMIBP")

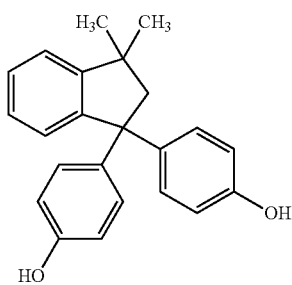

formula (II)

Step 1: Preparation of 3,3-dimethyl-indan-1-one

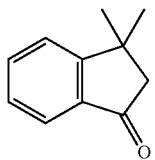

A solution of 25.0 g (0.25 moles) of 3,3-dimethyl acrylic acid in 250 ml of benzene was cooled to 0° C. in an ice bath. To this solution, 99 g (0.75 moles) of anhydrous aluminum chloride was slowly added using a spatula over a period of 20 minutes with stirring, after which the ice bath was removed and the reaction mixture was gradually heated to reflux. The reaction mixture was refluxed for ~7-8 h, then excess benzene was distilled off and the mixture was quenched with ice-cold dilute hydrochloric acid (HCl). The mixture was then diluted with ethylacetate (100 ml), the organic layer was separated and the aqueous layer was again washed with ethyl acetate (50 ml). The combined organic layer was washed with water (3×100 ml) until the pH was neutral, and then dried over anhydrous sodium sulfate and concentrated under vacuum. 43.0 g of reddish brown liquid was obtained, which was distilled under vacuum to give 29 g of the desired product, 3,3-dimethyl-indan-1-one (distilled at 82-84° C. at ~10 mm). Yield=73%, purity=99%. $^1$H NMR (DMSO-$d_6$, 300 MHz): δ 7.3-7.8 (m, 4H, Ar—H), δ 2.5 (s, 2H, O=C—CH$_2$), δ 1.3 (s, 6H, —CH$_3$). LC/MS: 161 (M+1).

Step 2: Preparation of 4,4'-(3,3-dimethyl-2,2-dihydro-1H-indene-1,1-diyl)diphenol

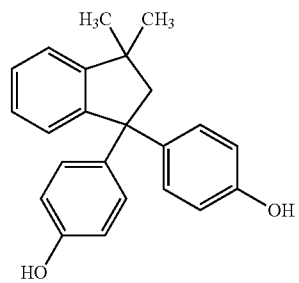 [SMILES: CC1(C)CC(c2ccc(O)cc2)(c2ccc(O)cc2)c2ccccc21]

To a 500 ml 2 necked round bottom flask (RBF) equipped with nitrogen inlet and water condenser, was charged 30.0 g (0.185 moles) of 3,3-dimethyl-indan-1-one from Step 1, 88.2 g (0.937 moles) of phenol, and 3.6 g (3 wt. % of total weight of reactants) of 3-MPA. The reaction mixture was stirred and to this 9.0 g (7 wt. % of total weight of reactants) of concentrated $H_2SO_4$ was added dropwise (~45 minutes), maintaining the temperature of the reaction mixture between 30-35° C. After complete addition of concentrated $H_2SO_4$, the temperature was raised to 55° C. and stirring was continued for 14 hours. The reaction mixture became a light orange/pink slurry. Into this slurry, 125 ml of toluene was added, and the reaction mixture was stirred at 55° C. for 2 hours (h). Then the mixture was cooled to room temperature and stirred for another 4 hours. A solid precipitated from the reaction mixture, and was then filtered by suction and washed with toluene (~100 ml) until the washings were colorless, and then also was washed with a sufficient amount of demineralized (DM) water (~150 ml) until the filtrate was colorless. The solid was then dried in an oven for 8 hours at 90° C. to provide 55 g of the desired product, 4,4'-(3,3-dimethyl-2,2-dihydro-1H-indene-1,1-diyl)diphenol. Yield=88% (HPLC area %), purity=99.3% (HPLC area %). Melting Point (MP)=236° C. $^1$H NMR (DMSO-$d_6$, 300 MHz): δ 9.2 (s, 2H, Ar—OH), δ 7.3-7.1 (m, 3H, Ar—H), δ 6.9-6.8 (m, 5H, Ar—H), δ 6.7-6.6 (d, 4H, Ar—H), δ 2.7 (s, 2H, O=C—CH$_2$), δ 1.2 (s, 6H, —CH$_3$).

Example 2

DMIBP-BPA Copolymer (PL-10-197)

A solution of 4,4'-(3,3-dimethyl-2,2-dihydro-1H-indene-1,1-diyl)diphenol ("DMIBP") was prepared by dissolving 8.11 g (0.0245 moles) DMIBP monomer (prepared according to Example 1) in 33% aqueous caustic (4.712 g) and water (30 ml). To a 2 L glass reactor equipped with a pH probe, condenser, agitator, phosgene inlet, and caustic scrubber was added methylene chloride (400 ml), deionized water (140 ml), triethylamine (0.11 ml, 0.0008 moles), bisphenol-A (BPA, 11.89 g, 0.0522 moles), p-cumylphenol (0.59 g, 0.0028 moles), and the DMIBP solution. The batch was phosgenated in excess at a rate of 2 grams per min for 8 minutes, maintaining the pH between 9 and 10 with concomitant caustic addition (33% w/w). At the completion of the phosgenation, an additional 0.10 ml of triethylamine was added to the reaction to quench unwanted chloroformates. The reactor was purged with nitrogen to remove excess phosgene. The reaction mixture was extracted with dilute acid (1N HCl) and deionized water. The final product of DMIBP-BPA Copolymer (PL-10-197) was isolated as a white powder by exposing the polymer solution (in methylene chloride) to hot water, evaporating the solvent and providing a white powder. Characterization data for the DMIBP-BPA Copolymer (PL-10-197) is provided in Table 1, shown below.

Example 3

DMIBP-BPA Copolymer (PL-10-212)

A solution of DMIBP was prepared by dissolving 10.85 g (0.0328 moles) DMIBP monomer (prepared according to Example 1) in 33% aqueous caustic (8.3 g) and water (30 ml). To a 2 L glass reactor equipped with a pH probe, condenser, agitator, phosgene inlet, and caustic scrubber was added methylene chloride (400 ml), deionized water (140 ml), triethylamine (0.20 ml, 0.0015 moles), bisphenol-A (BPA, 9.15 g, 0.0401 moles), p-cumylphenol (0.46 g, 0.0022 moles), and DMIBP solution. The batch was phosgenated in excess at a rate of 2 grams per min for 8 minutes, maintaining the pH between 9 and 10 with concomitant caustic addition (33% w/w). At the completion of the phosgenation, the reactor was purged with nitrogen to remove excess phosgene. The reaction mixture was extracted with dilute acid (1N HCl) and deionized water. The final product DMIBP-BPA Copolymer (PL-10-212) was isolated as a white powder by exposing the polymer solution (in methylene chloride) to hot water, evaporating the solvent and providing a white powder. Characterization data for the DMIBP-BPA Copolymer (PL-10-212) is provided in Table 1, shown below.

Example 4

DMIBP-BPA Copolymer (PL-10-227)

A solution of DMIBP was prepared by dissolving 10.23 g (0.0310 moles) DMIBP monomer (prepared according to Example 1) in 33% aqueous caustic (8.3 g) and water (30 ml). To a 2 L glass reactor equipped with a pH probe, condenser, agitator, phosgene inlet, and caustic scrubber was added methylene chloride (400 ml), deionized water (140 ml), triethylamine (0.16 ml, 0.0011 moles), bisphenol-A (BPA, 5.77 g, 0.0253 moles), p-cumylphenol (0.36 g, 0.0017 moles), and DMIBP solution. The batch was phosgenated in excess at a rate of 2 grams per min for 8 minutes, maintaining the pH between 9 and 10 with concomitant caustic addition (33% w/w). At the completion of the phosgenation, the reactor was purged with nitrogen to remove excess phosgene. The reaction mixture was extracted with dilute acid (1N HCl) and deionized water. The final product DMIBP-BPA Copolymer (PL-10-227) was isolated as a white powder by exposing the polymer solution (in methylene chloride) to hot water, evaporating the solvent and providing a white powder. Characterization data for the DMIBP-BPA Copolymer (PL-10-227) is provided in Table 1, shown below.

Example 5

DMIBP-BPA Copolymer (PL-11-004)

A solution of DMIBP was prepared by dissolving 11.67 g (0.0353 moles) DMIBP monomer (prepared according to Example 1) in 33% aqueous caustic (10 g) and water (30 ml). To a 2 L glass reactor equipped with a pH probe, condenser, agitator, phosgene inlet, and caustic scrubber was added methylene chloride (500 ml), deionized water (140 ml), triethylamine (0.15 ml, 0.0011 moles), bisphenol-A (BPA, 4.33 g, 0.0190 moles), p-cumylphenol (0.35 g, 0.0016 moles), and DMIBP solution. The batch was phosgenated in excess at a rate of 2 grams per min for 8 minutes, maintaining pH between 9 and 10 with concomitant caustic addition (33% w/w). At the completion of the phosgenation, an additional 0.1 ml of triethylamine was added to the reaction mixture to quench unwanted chloroformates and the reaction was rephosgenated for 2 minutes at a rate of 2 grams per minute. The reactor was purged with nitrogen to remove excess phosgene. The reaction mixture was extracted with dilute acid (1N HCl) and deionized water. The final product DMIBP-BPA Copolymer (PL-11-004) was isolated as a white powder by exposing the polymer solution (in methylene chloride) to hot water, evaporating the solvent and providing a white powder. Characterization data for the DMIBP-BPA Copolymer (PL-11-004) is provided in Table 1, shown below.

Example 6

DMIBP Homopolymer (PL-11-005)

A solution of DMIBP was prepared by dissolving 16.00 g (0.0484 moles) DMIBP monomer (prepared according to Example 1) in 33% aqueous caustic (15 g) and water (30 ml). To a 2 L glass reactor equipped with a pH probe, condenser, agitator, phosgene inlet, and caustic scrubber was added methylene chloride (500 ml), deionized water (140 ml), triethylamine (0.13 ml, 0.0010 moles), p-cumylphenol (0.31 g, 0.0015 moles), and DMIBP solution. The batch was phosgenated in excess at a rate of 2 grams per min for 8 minutes, maintaining the pH between 9 and 10 with concomitant caustic addition (33% w/w). At the completion of the phosgenation, the reactor was purged with nitrogen to remove excess phosgene. The reaction mixture was extracted with dilute acid (1N HCl) and deionized water. The final product DMIBP Homopolymer (PL-11-005) was isolated as a white powder by exposing the polymer solution (in methylene chloride) to hot water, evaporating the solvent and providing a white powder. Characterization data for the DMIBP Homopolymer (PL-11-005) is provided in Table 1, shown below.

Example 7

4,4'-(3-methyl-2,2,3-trihydro-1H-indene-1,1-diyl)diphenol ("MIBP")

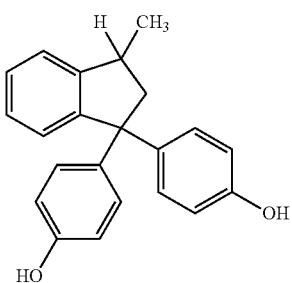

formula (III)

Step 1: Preparation of 3-methyl-indan-1-one

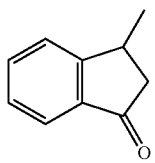

A solution of crotonic acid (20 g, 0.232 moles) in benzene (147 ml) was added AlCl$_3$ (93 g, 0.748 moles) and the mixture was refluxed for 7 hours. Completion of the reaction was monitored by HPLC & GC. Excess benzene was distilled off and the reaction mixture was poured slowly into ice cold HCl. The organic compound was extracted with ethylacetate. The organic phase was washed thoroughly with water, dried, and evaporated under vacuum. The resultant oil was purified by high vacuum distillation (90-94° C. at ~2 mm) giving 25 g (74%) of 99.2% pure 3-methyl-indan-1-one.

Step 2: Preparation of 4,4'-(3-methyl-2,2,3-trihydro-1H-indene-1,1-diyl)diphenol

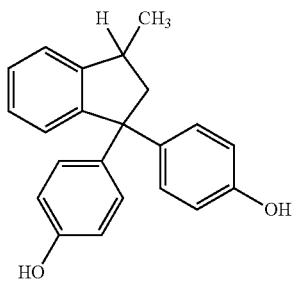 [SMILES: CC1CC(c2ccc(O)cc2)(c2ccc(O)cc2)c2ccccc21]

To a 500 ml 3 necked RBF equipped with an overhead stirrer, gas bubbler, and water condenser was charged 3-methyl-indan-1-one (20 g, 0.136 moles), phenol (128 g, 1.36 moles) and 3-MPA (2.528 g, 3 wt % with regard to the reaction mixture). The reaction mixture was initially stirred at room temperature and dry HCl was bubbled through the mixture. After 0.5 hour, HCl bubbling was stopped, the bath temperature was gradually increased to 35° C. and the reaction mixture was continually stirred at that temperature for 10 hours. After completion of 10 hours, 100 ml of toluene was added to the reddish brown viscous mass and the resultant mixture was washed with water (2×50 ml), saturated NaHCO$_3$ (2×50 ml), water, and then dried over anhydrous Na$_2$SO$_4$. The remaining solvent was then removed under vacuum. The residue obtained was subjected to vacuum distillation (50° C. at 1 mm) to remove excess (unreacted) phenol. A dark brown residue was obtained after distilling excess phenol. The residue was dissolved in 20% NaOH (200 ml). The insolubles were filtered off and the resultant filtrate was acidified with dilute HCl. A solid precipitated from the reaction mixture, which was filtered and washed thoroughly with water until chloride free. The solid was then dried to provide 25 g of a solid. The solid was suspended in toluene (50 ml) and the resultant mixture was heated to reflux for 1 hour. After 1 hour, the mixture was cooled to room temperature and stirred for another 4 hours. A solid precipitated, was filtered, washed with hot toluene (1 wt/vol.), and dried to provide 10 g of the desired product, 4,4'-(3-methyl-2,2,3-trihydro-1H-indene-1,1-diyl)diphenol, with purity of 99.25%. MP=165.75° C. $^1$H NMR (DMSO-d$_6$, 300 MHz): δ 9.2 (s, 2H, Ar—OH), δ 7.3-7.1 (m, 3H, Ar—H), δ 7.0-6.8 (m, 5H, Ar—H), δ 6.7-6.6 (m, 4H, Ar—H), δ 3.0-2.8 (m, 2H, —CH$_2$), δ 2.2-2.1 (m, 1H, —CH$_2$).

Example 8

MIBP-BPA Copolymer (PL-11-116)

A solution of MIBP was prepared by dissolving (5.32 g, 0.0168 moles) MIBP monomer (prepared according to Example 7) in 33% aqueous caustic (7 g) and water (30 mL). To a 2 L glass reactor equipped with pH probe, condenser, agitator, phosgene inlet, and caustic scrubber was added methylene chloride (500 mL), deionized water (140 mL), bisphenol-A (4.68 g, 0.0205 moles), triethylamine (0.10 mL, 0.0007 moles), p-cumylphenol (0.24 g, 0.0011 moles), and MIBP solution. The batch was phosgenated in excess at a rate of 2 grams per min for 2 minutes, maintaining the pH between 9 and 10 with concomitant caustic addition (33% w/w). At the completion of the phosgenation, the reactor was purged with nitrogen to remove excess phosgene. The reaction mixture extracted with dilute acid (1N HCl) and deionized water. The final product was isolated as a white powder by exposing the polymer solution (in methylene chloride) to hot water, evaporating the solvent and providing a white powder. Characterization data for the MIBP-BPA Copolymer (PL-11-116) is provided in Table 1, shown below.

Example 9

4,4'-(2,3-dihydro-1H-indene-1,1-diyl)diphenol ("IBP")

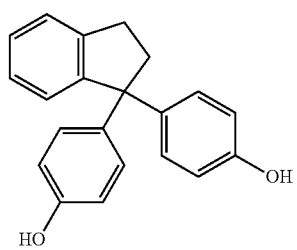

(40)

A 500 ml 3 necked RBF equipped with a overhead stirrer, gas bubbler and a water condenser, was charged with indanone (40 g, 0.302 mol.), phenol (142.1 g, 1.51 mol.) and 3-MPA (5.48 g, 3 wt % wrt reaction mixture). The reaction mixture was initially stirred at room temperature and dry HCl was bubbled through the mixture. While continuing the HCl bubbling, the bath temperature was gradually increased to 50° C. After 1 hour, HCl bubbling was stopped and the reaction mixture was continued to stir at 50° C. for 7 hours. After completion of 7 hours, 90 ml of toluene was added to the reddish brown viscous mass and the resultant mixture was stirred at same temperature for 2 hours. Then it was cooled to room temperature and stirred for another 4 hours. A solid precipitated from reaction mixture, and was then filtered by suction and washed with toluene (~70 ml) until the washing were colorless, and then also was washed with a sufficient amount of DM water (~100 ml) until the filtrate was colorless. The solid was then dried in an oven for 8 hours at 90° C. Crude yield=45 g, Purity=98.7% (HPLC area %).

45 g of crude IBP was dissolved in 20% NaOH (200 ml). The insolubles were filtered off and the resultant filtrate was acidified with dilute HCl to provide a precipitated solid. The precipitated solid was filtered, washed thoroughly with water until chloride free, and dried. Yield=28 g. The 28 g of solid was dissolved in MeOH (168 ml), 2.8 g (10 wt %) of activated charcoal was added and the resultant mixture was heated to reflux for 1 hour. The charcoal was filtered and washed thoroughly with hot MeOH (42 ml). To the filtrate, water (85 ml) was added to precipitate the pure product, 4,4'-(2,3-dihydro-1H-indene-1,1-diyl)diphenol ("IBP"). The mixture was allowed to stand at room temperature for about 5 h. Complete precipitation of IBP was ensured by cooling the mixture (to 0° C.) in ice for 2 hours. Precipitated IBP solid was filtered, washed with an ice cold MeOH:water (50:50) solvent system (1 wt/vol.), and dried. 26 g of pure IBP with a purity of 99.55% (HPLC area %) was obtained. MP=218° C. $^1$H NMR (DMSO-d$_6$, 300 MHz): δ 9.2 (s, 2H, Ar—OH), δ 7.3-6.9 (m, 4H, Ar—H), δ 6.8 (m, 4H, Ar—H), δ 6.6 (m, 4H, Ar—H), δ 2.8 (m, 2H, —CH$_2$), δ 2.6 (m, 2H, —CH$_2$).

Comparative Example 10

IBP-BPA Copolymer (PL-11-058)

A solution of 4,4'-(2,3-dihydro-1H-indene-1,1-diyl)diphenol ("IBP") was prepared by dissolving 8.33 g (0.0275 moles) of IBP monomer (prepared according to Example 9) in 33% aqueous caustic (15 g) and water (30 ml). To a 2 L glass reactor equipped with a pH probe, condenser, agitator, phosgene inlet, and caustic scrubber was added methylene chloride (500 ml), deionized water (140 ml), triethylamine (0.17 ml, 0.0012 moles), bisphenol-A (7.67 g, 0.0337 moles), p-cumylphenol (0.39 g, 0.0018 moles), and IBP solution. The batch was phosgenated in excess at a rate of 2 grams per min for 4 minutes, maintaining the pH between 9 and 10 with concomitant caustic addition (33% w/w). At the completion of the phosgenation, the reactor was purged with nitrogen to remove excess phosgene and the reaction mixture extracted with dilute acid (1N HCl) and deionized water. The final product IBP-BPA Copolymer (PL-11-058) was isolated as a white powder by exposing the polymer solution (in methylene chloride) to hot water, evaporating the solvent and providing a white powder. Characterization data for the IBP-BPA Copolymer (PL-11-058) is provided in Table 1, shown below.

Comparative Example 11

IBP Homopolymer (PL-11-059)

A solution of IBP was prepared by dissolving 10.00 g (0.0331 moles) of IBP monomer (prepared according to Example 9) in 33% aqueous caustic (15 g) and water (30 ml). To a 2 L glass reactor equipped with a pH probe, condenser, agitator, phosgene inlet, and caustic scrubber was added methylene chloride (500 ml), deionized water (140 ml), triethylamine (0.09 ml, 0.0007 moles), p-cumylphenol (0.21 g, 0.0010 moles), and IBP solution. The batch was phosgenated in excess at a rate of 2 grams per min for 2 minutes, maintaining the pH between 9 and 10 with concomitant caustic addition (33% w/w). At the completion of the phosgenation, the reactor was purged with nitrogen to remove excess phosgene and the reaction mixture extracted with dilute acid (1N HCl) and deionized water. The final product of IPB Homopolymer (PL-11-059) was isolated as a white powder by exposing the polymer solution (in methylene chloride) to hot water, evaporating the solvent and providing a white powder. Characterization data for the IBP Homopolymer (PL-11-059) is provided in Table 1, shown below.

Comparative Example 12

PPPBP-BPA Copolymer (PL-10-196)

A solution of 3,3-bis(4-hydroxyphenyl)-2-phenylisoindolin-1-one ("PPPBP") was prepared by dissolving PPPBP monomer (8.96 g, 0.0228 moles) in 33% aqueous caustic (4.712 g) and water (30 ml). To a 2 L glass reactor equipped with a pH probe, condenser, agitator, phosgene inlet, and caustic scrubber was added methylene chloride (400 ml), deionized water (140 ml), triethylamine (0.10 ml, 0.0007 moles), bisphenol-A (BPA, 11.04 g, 0.0484 moles), p-cumylphenol (0.54 g, 0.0026 moles), and PPPBP solution. The batch was phosgenated in excess at a rate of 2 grams per min for 8 minutes, maintaining the pH between 9 and 10 with concomitant caustic addition (33% w/w). At the completion of the phosgenation, the reactor was purged with nitrogen to remove excess phosgene and the reaction mixture extracted with dilute acid (1N HCl) and deionized water. The final product PPPBP-BPA Copolymer (PL-10-196) was isolated as a white powder by exposing the polymer solution (in methylene chloride) to hot water, evaporating the solvent and providing a white powder. Characterization data for the PPPBP-BPA Copolymer (PL-10-196) is provided in Table 1, shown below.

Characterization Data and Mapping of Tg

Table 1, shown below, provides characterization data for the polymers of Examples 2-6, 8, and 10-12. Table 1 also summarizes the copolymer DMIBP loading versus glass transition temperatures for a series of DMIBP copolycarbonates in comparison with the Comparative Examples 10, 11, and 12. A higher mol % loading of DMIBP (>55 mole %) is required to achieve similar Tg as Comparative Example 12 (33 mole %). Also shown is comparison of molecular weight analyzed on both reaction samples ("Reaction") and on isolated product post-drying ("Powder").

TABLE 1

| | PL # | | | | | | | | |
|---|---|---|---|---|---|---|---|---|---|
| | 10-197 | 10-212 | 10-227 | 11-004 | 11-005 | 11-116 | 11-058 | 11-059 | 10-196 |
| | | | | | Example | | | | |
| | 2 | 3 | 4 | 5 | 6 | 8 | 10 (Comp) | 11 (Comp) | 12 (Comp) |
| Powder | | | | | | | | | |
| Mw | 17,087 | | 19,964 | 20,533 | 18,780 | 22,477 | 37,856 | 27,763 | |
| Mn | 6,325 | | 6,616 | 7,243 | 3,909 | 5,958 | 4,532 | 6,839 | |
| PDI | 2.70 | | 3.02 | 2.83 | 4.80 | 3.77 | 8.35 | 3.91 | |
| Tg | 168.1 | 179.83 | 186.9 | 189.8 | 209 | 182.2 | 175.33 | 204.4 | 195.1 |
| Cp | 0.3 | 0.3976 | 0.3 | 0.3 | 0.4 | 0.4 | 0.4 | 0.4 | 0.4 |
| Target mole % monomer | 32% DMIBP | 45% DMIBP | 55% DMIBP | 65% DMIBP | 100% DMIBP | 45% MIBP | 45% IBP | 100% IBP | 32% PPPBP |
| Reaction | | | | | | | | | |
| Mw | 17,466 | 23,413 | 20,318 | 21,029 | 20,140 | 23,303 | 38,956 | 26,980 | 23,374 |
| Mn | 6609 | 6,724 | 6,169 | 7,042 | 4,094 | 6,846 | 4,967 | 6,956 | 7,954 |
| PDI | 2.64 | 3.48 | 3.29 | 2.99 | 4.92 | 3.40 | 7.84 | 3.88 | 2.94 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A polymer comprising repeating units of formula (1),

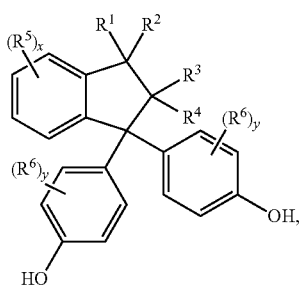

wherein
$R^1$ is $C_1$-$C_6$ alkyl, $C_3$-$C_8$ cycloalkyl, aryl, or arylalkyl;
$R^2$ is $C_1$-$C_6$ alkyl, $C_3$-$C_8$ cycloalkyl, aryl, or arylalkyl;
$R^3$ is hydrogen, $C_1$-$C_6$ alkyl, $C_3$-$C_8$ cycloalkyl, aryl, or arylalkyl;
$R^4$ is hydrogen, $C_1$-$C_6$ alkyl, $C_3$-$C_8$ cycloalkyl, aryl, or arylalkyl;
$R^5$ and $R^6$, at each occurrence, are each independently halogen, $C_1$-$C_6$ alkyl, or $C_3$-$C_8$ cycloalkyl; and
x and y, at each occurrence, are each independently 0, 1, 2, 3, or 4;
wherein the polymer further comprises:
(i) repeating units derived from one or more monomers having the structure HO-$A_1$-$Y_1$-$A_2$-OH wherein each of $A_1$ and $A_2$ comprise a monocyclic divalent arylene group, and $Y_1$ is a bridging group having one or more atoms;
(ii) repeating units derived from one or more monomers having the structure

wherein each $R^h$ is independently a halogen atom, a $C_1$-$C_{10}$ hydrocarbyl, or a halogen substituted $C_1$-$C_{10}$ hydrocarbyl, and n is 0 to 4; or
(iii) one or more polyester repeating units having the structure

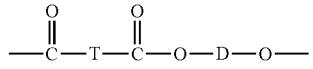

wherein D comprises one or more alkyl containing $C_6$-$C_{20}$ aromatic group(s), or one or more $C_6$-$C_{20}$ aromatic group(s), and T comprises a $C_6$-$C_{20}$ aromatic group;
wherein the repeating units of (i), (ii), and (iii) are different from the repeating units of formula (1).

2. The polymer of claim 1, wherein the repeating units of formula (1) are derived from a monomer of formula (II),

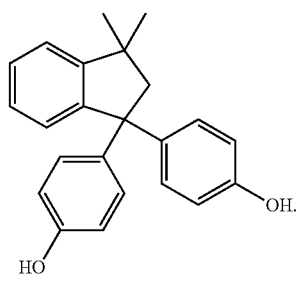

3. The polymer of claim 1, wherein the polymer is free of halogen atoms.

4. The polymer of claim 1, comprising an end cap group, wherein at least one end cap group is derived from p-cumylphenol, t-butylphenol, 4-hydroxybenzonitrile, or phenol.

5. The polymer of claim 1, having a weight average molecular weight ranging from about 15,000 to about 50,000 g/mol [±1,000 g/mol].

6. The polymer of claim 1, having a polydispersity ranging from about 2.0 to about 7.0.

7. The polymer of claim 1, having a glass transition temperature ranging from about 150° C. to about 220° C.

8. The polymer of claim 1, comprising repeating units derived from 2,2-bis(4-hydroxyphenyl)propane (bisphenol-A).

9. The polymer of claim 1, wherein the polymer comprises more than 15 mole percent repeating units of formula (1).

10. The polymer of claim 1, wherein the polymer comprises more than 15 mole percent repeating units of formula (1), and the remainder of the structural units are derived from 2,2 bis(4-hydroxyphenyl)propane (bisphenol-A).

11. The polymer of claim 1, made by a melt process or an interfacial polymerization process.

12. An article comprising the polymer of claim 1.

13. The article of claim 12, wherein the article has a glass transition temperature (Tg) of at least 160° C.

14. The article of claim 12, selected from at least one of the following: automotive bumpers, other automotive exterior components, automobile mirror housings, automobile wheel covers, automobile instrument panels and trim, automobile glove boxes, automobile door hardware and other interior trim, automobile exterior lights, automobile parts within the engine compartment, plumbing equipment, valves and pumps, air conditioning heating and cooling parts, furnace and heat pump parts, computer parts, electronics parts, projector parts, electronic display parts, copier parts, scanner parts, electronic printer toner cartridges, hair driers, irons, coffee makers, toasters, washing machines, microwaves, ovens, power tools, electric components, lighting parts, dental instruments, medical instruments, cookware, medical instrument trays, animal cages, fibers, laser welded medical devices, fiber optics, lenses (auto and non-auto), cell phone parts, greenhouse components, sun room components, and fire helmets.

15. A blend composition, comprising:
(i) a first polymer (A) containing repeating units derived from a monomer of formula (I),

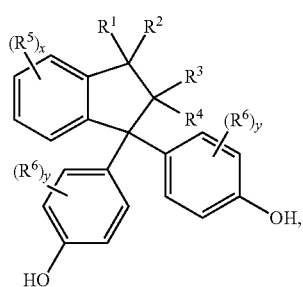

(I)

wherein
$R^1$ is $C_1$-$C_6$ alkyl, $C_3$-$C_8$ cycloalkyl, aryl, or arylalkyl;
$R^2$ is $C_1$-$C_6$ alkyl, $C_3$-$C_8$ cycloalkyl, aryl, or arylalkyl;
$R^3$ is hydrogen, $C_1$-$C_6$ alkyl, $C_3$-$C_8$ cycloalkyl, aryl, or arylalkyl;
$R^4$ is hydrogen, $C_1$-$C_6$ alkyl, $C_3$-$C_8$ cycloalkyl, aryl, or arylalkyl;
$R^5$ and $R^6$, at each occurrence, are each independently halogen, $C_1$-$C_6$ alkyl, or $C_3$-$C_8$ cycloalkyl; and
x and y, at each occurrence, are each independently 0, 1, 2, 3, or 4; and
(ii) a second polymer (B) which is different from polymer (A).

16. The blend composition of claim 15, wherein the monomer of formula (I) is 4,4'-(3,3-dimethyl-2,2-dihydro-1H-indene-1,1-diyl)diphenol.

17. The blend composition of claim 15, wherein polymer (A) is a copolycarbonate of 4,4'-(3,3-dimethyl-2,2-dihydro-1H-indene-1,1-diyl)diphenol and bisphenol-A.

18. The blend composition of claim 15, wherein polymer (B) is derived from monomer units other than monomer units of formula (I).

19. The blend composition of claim 15, wherein polymer (B) is selected from at least one of the following: a vinyl polymer, a rubber-modified graft copolymer, an acrylic polymer, polyacrylonitrile, a polystyrene, a polyolefin, a polyester, a polyesteramide, a polysiloxane, a polyurethane, a polyamide, a polyamideimide, a polysulfone, a polyepoxide, a polyether, a polyimide, a polyetherimide, a polyphenylene ether, a polyphenylene sulfide, a polyether ketone, a polyether ether ketone, an ABS resin, an ASA resin, a polyethersulfone, a polyphenylsulfone, a poly(alkenylaromatic) polymer, a polybutadiene, a polyacetal, a polycarbonate, a polyphenylene ether, an ethylene-vinyl acetate copolymer, a polyvinyl acetate, a liquid crystal polymer, an ethylene-tetrafluoroethylene copolymer, an aromatic polyester, a polyvinyl fluoride, a polyvinylidene fluoride, a polyvinylidene chloride, tetrafluoroethylene, a polylactide, a polylactic acid (PLA), a polycarbonate-polyorganosiloxane block copolymer, and a copolymer comprising: (i) an aromatic ester, (ii) an estercarbonate, and (iii) carbonate repeat units.

20. The blend composition of any one of claim 15, further comprising at least one additive.

21. The blend composition of claim 20, wherein the additive is an impact modifier selected from at least one of the following: polycarbonate-polysiloxane copolymers, acrylonitrile-butadiene-styrene (ABS) polymers, methacrylate-butadiene-styrene (MBS) polymers, and acrylate polymers.

22. The blend composition of claim 21, wherein the impact modifier is a polycarbonate-polysiloxane copolymer.

23. The blend composition of claim 21, wherein the impact modifier is a combination of a polycarbonate-polysiloxane copolymer and an acrylate polymer.

24. The blend composition of claim 20, wherein the additive is a UV stabilizer selected from 2-(2'-hydroxyphenyl)-benzotriazoles.

25. The blend composition of claim 24, wherein the UV stabilizer is 2-(2H-benzotriazole-2-yl)-4,6-bis(1-methyl-1-phenyl-ethyl)phenol.

26. An article comprising the blend composition of claim 15.

27. The article of claim 26, selected from at least one of the following: automotive bumpers, other automotive exterior components, automobile mirror housings, automobile wheel covers, automobile instrument panels and trim, automobile glove boxes, automobile door hardware and other interior trim, automobile exterior lights, automobile parts within the engine compartment, plumbing equipment, valves and pumps, air conditioning heating and cooling parts, furnace and heat pump parts, computer parts, electronics parts, projector parts, electronic display parts, copier parts, scanner parts, electronic printer toner cartridges, hair driers, irons, coffee makers, toasters, washing machines, microwaves, ovens, power tools, electric components, lighting parts, dental instruments, medical instruments, cookware, medical instrument trays, animal cages, fibers, laser welded medical devices, fiber optics, lenses (auto and non-auto), cell phone parts, greenhouse components, sun room components, and fire helmets.

28. The composition of claim 1, wherein $R^1$ is methyl; $R^2$ is methyl; $R^3$ is hydrogen; $R^4$ is hydrogen; x is 0; and y is 0.

29. The polymer of claim 1, wherein the polymer comprises about 15 mole percent to about 85 mole percent of repeating units of formula (1).

30. The polymer of claim 1, wherein the polymer comprises about 55 mole percent or greater of repeating units of formula (1).

31. The polymer of claim 1, having a glass transition temperature ranging from about 170° C. to about 220° C.

* * * * *